(12) United States Patent
Cheng et al.

(10) Patent No.: US 7,163,819 B2
(45) Date of Patent: Jan. 16, 2007

(54) BACTERIAL HEMOGLOBIN GENES AND THEIR USE TO INCREASE CAROTENOID PRODUCTION

(75) Inventors: Qiong Cheng, Wilmington, DE (US); Michael P. Perry, Landenberg, PA (US); Luan Tao, Havertown, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/397,745

(22) Filed: Apr. 4, 2006

(65) Prior Publication Data

US 2006/0234334 A1 Oct. 19, 2006

Related U.S. Application Data

(60) Provisional application No. 60/671,449, filed on Apr. 14, 2005.

(51) Int. Cl.
*C12P 21/02* (2006.01)
*C12P 1/00* (2006.01)
*C12N 15/31* (2006.01)
*C12N 15/67* (2006.01)

(52) U.S. Cl. ............... 435/252.3; 435/67; 435/41; 435/91; 435/70.1; 435/69.1; 435/70.2; 435/320.1; 435/254.1; 435/256.7; 435/251.2; 435/254.2; 435/254.3; 435/254.6; 435/254.22; 435/253.1; 435/252.8; 435/252.1; 435/252.31

(58) Field of Classification Search ............ 435/252.3, 435/67, 41, 70.1, 320.1, 252.1, 254.1, 257.1; 536/23.2
See application file for complete search history.

(56) References Cited

U.S. PATENT DOCUMENTS

| | | |
|---|---|---|
| 5,049,493 A | 9/1991 | Khosla et al. |
| 6,825,002 B1 | 11/2004 | Tsubokura et al. |
| 6,984,523 B1 | 1/2006 | Cheng et al. |
| 7,091,031 B1 | 8/2006 | Cheng et al. |
| 2005/0227311 A1 | 10/2005 | Cheng et al. |

OTHER PUBLICATIONS

Zelasco et al. Expression of the Vitreoscilla Hemoglobin (VHb)-Encoding Gene in Transgenic White Poplar. Plant Growth and Biomass Production, Biochemical Characterization and Cell Survival under Submergence, Oxidative and Nitrosative Stress Conditions. Molecular Breeding (2006) vol. 17 :201-216.*
Philip S. Tsai,et al Effect of Vitreoscilla hemoglobin dosage on microaerobic *Escherichia coli* carbon and energy metabolism Biotechnology and Bioengineering. vol. 49, Issue 2, pp. 139-150 Published Online: Mar. 26, 2000.*
Christian J.T. Bollinger et. al., Novel Hemoglobins to Enhance Microaerobic Growth and Substrate Utilization in *Escherichia coli*, Biotechnol., Prog., 2001, vol. 17:798-808.
Jonathan B. Wittenberg et. al, Truncated Hemoglobins: A New Family of Hemoglobins Widely Distributed in Bacteria, Unicellular Eukaryotes, and Plants, The Journal of Biological Chemistry, 2002, vol. 277:871-874.
N. Ward et. al., Genomic Insights into Methanotrophy; The Complete Genome Sequence of Methylococcus Capsulatus (Bath), PLoS Biol., 2004, vol. 2:1616-1628.
G. Armstrong, Carotenoid Genetics and Biochemistry, Comprehensive Natural Products Chemistry, 1999, vol. 2:321-352.
P. Lee et. al., Metabolic Engineering Towards Biotechnological Production of Carotenoids in Microorganisms, Appl. Microbiol. Biotechnol., 2002, vol. 60:1-11.
Lee et. al., Biosynthesis of Structurally Novel Carotenoids in *Escherichia coli*, Chem. Biol., 2003, vol. 10:453-462.
P. Fraser et. al., The Biosynthesis and Nutritional Uses of Carotenoids, Progress in Lipid Research, 2004, vol. 43:228-265.
A.D. Frey et. al., Bacterial Hemoglobins and Flavohemoglobins: Versatile Proteins and Their Impact on Microbiology and Biotechnology, FEMS Microbiol. Rev., 2003, vol. 27:525-545.
Pathania et. al., Mycobacterium Tuberculosis Hemoglobin HBO Associates with Membranes and Stimulates Cellular Respiration of Recombinant *Escherichia coli*, J. Biol. Chem., 2002, vol. 277:15293-15302.

* cited by examiner

*Primary Examiner*—Rebecca E. Prouty
*Assistant Examiner*—Kagnew Gebreyesus

(57) ABSTRACT

Genes encoding bacterial oxygen binding proteins are provided. Recombinant expression of at least one of the present bacterial hemoglobin genes increased the growth characteristics and/or carotenoid production levels in microbial host cells grown under microaerobic conditions.

8 Claims, 8 Drawing Sheets

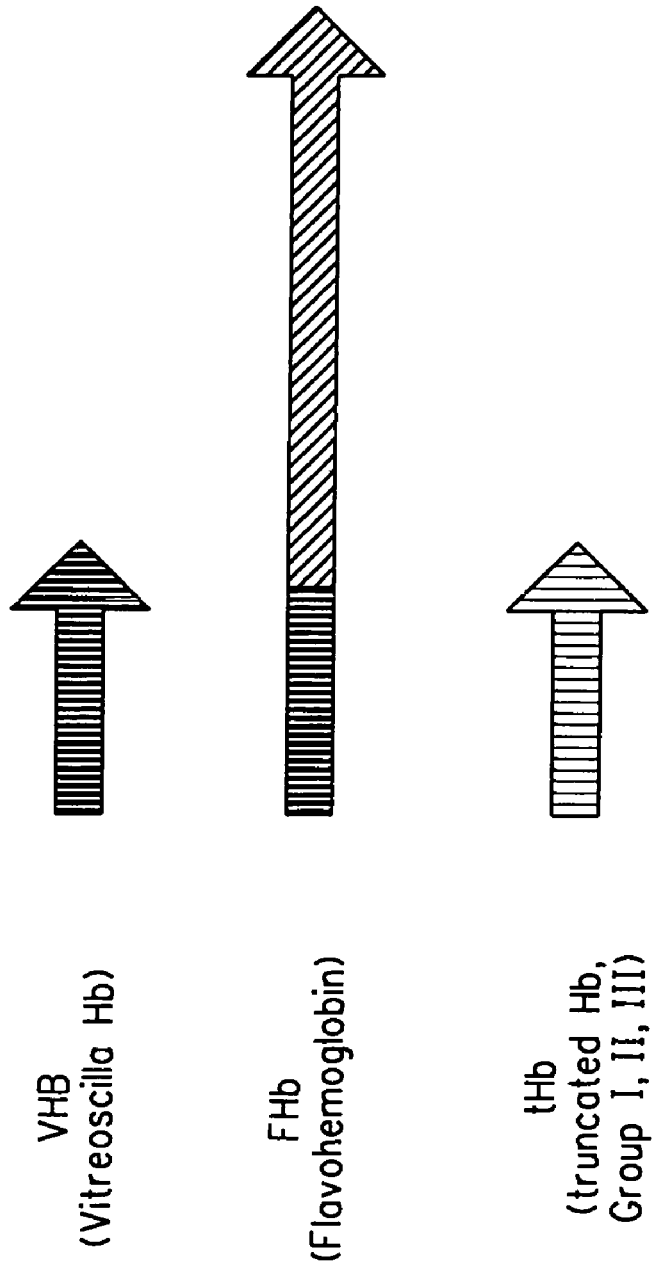

SEQUENCE LISTING

```
<160> NUMBER OF SEQ ID NOS: 24

<210> SEQ ID NO 1
<211> LENGTH: 378
<212> TYPE: DNA
<213> ORGANISM: Methylomonas sp. 16a
<220> FEATURE:
<221> NAME/KEY: CDS
<222> LOCATION: (1)..(378)

<400> SEQUENCE: 1 atg agt gca acc gct act acg ctg tat gaa caa tta ggc ggc gaa gcc      48
Met Ser Ala Thr Ala Thr Thr Leu Tyr Glu Gln Leu Gly Gly Glu Ala
1               5                   10                  15 gcc gta aat gcc gcc gta gac att ttt tat cga aaa gta ctg gat gat      96
Ala Val Asn Ala Ala Val Asp Ile Phe Tyr Arg Lys Val Leu Asp Asp
            20                  25                  30 cac cgt atc aac cgt ttt ttc gat cac acc gat atg gaa aag cag gcg     144
His Arg Ile Asn Arg Phe Phe Asp His Thr Asp Met Glu Lys Gln Ala
        35                  40                  45 gcc aaa caa aaa gcc ttt tta acc atg gca ttc ggc ggc ccg aat aac     192
```

```
                Ala Lys Gln Lys Ala Phe Leu Thr Met Ala Phe Gly Gly Pro Asn Asn
                 50                  55                  60 tac agt ggc gcc gac atg cgc aga gga cac gcg cac ctg gtg aaa atg          240
Tyr Ser Gly Ala Asp Met Arg Arg Gly His Ala His Leu Val Lys Met
 65                  70                  75                  80 ggt ttg gat gat tcc cat ttc gat gct gta atg gaa cac ctg acc ggc          288
Gly Leu Asp Asp Ser His Phe Asp Ala Val Met Glu His Leu Thr Gly
                 85                  90                  95 acc ttg cgc gaa ctc aac gtg ccg caa aac ttg atc gac caa gtc gcg          336
Thr Leu Arg Glu Leu Asn Val Pro Gln Asn Leu Ile Asp Gln Val Ala
                100                 105                 110 gcc atc gcg gaa agc aca cgc acc gac gta ttg ggt cgc taa                  378
Ala Ile Ala Glu Ser Thr Arg Thr Asp Val Leu Gly Arg
                115                 120             125

<210> SEQ ID NO 2
<211> LENGTH: 125
<212> TYPE: PRT
<213> ORGANISM: Methylomonas sp. 16a

<400> SEQUENCE: 2

Met Ser Ala Thr Ala Thr Thr Leu Tyr Glu Gln Leu Gly Gly Glu Ala
 1               5                  10                  15

Ala Val Asn Ala Ala Val Asp Ile Phe Tyr Arg Lys Val Leu Asp Asp
                20                  25                  30

His Arg Ile Asn Arg Phe Phe Asp His Thr Asp Met Glu Lys Gln Ala
            35                  40                  45

Ala Lys Gln Lys Ala Phe Leu Thr Met Ala Phe Gly Gly Pro Asn Asn
 50                  55                  60

Tyr Ser Gly Ala Asp Met Arg Arg Gly His Ala His Leu Val Lys Met
 65                  70                  75                  80

Gly Leu Asp Asp Ser His Phe Asp Ala Val Met Glu His Leu Thr Gly
                 85                  90                  95

Thr Leu Arg Glu Leu Asn Val Pro Gln Asn Leu Ile Asp Gln Val Ala
                100                 105                 110

Ala Ile Ala Glu Ser Thr Arg Thr Asp Val Leu Gly Arg
            115                 120             125

<210> SEQ ID NO 3
<211> LENGTH: 381
<212> TYPE: DNA
<213> ORGANISM: Methylomonas sp. 16a
<220> FEATURE:
<221> NAME/KEY: CDS
<222> LOCATION: (1)..(381)

<400> SEQUENCE: 3 atg agc gaa gaa caa aaa gtc tct ctg tat gag cga atc ggc ggt gaa          48
Met Ser Glu Glu Gln Lys Val Ser Leu Tyr Glu Arg Ile Gly Gly Glu
 1               5                  10                  15 gca gcc gtc aat gcg gcg gtc gat ctt ttt tac gac aaa gta ctc aat          96
Ala Ala Val Asn Ala Ala Val Asp Leu Phe Tyr Asp Lys Val Leu Asn
                20                  25                  30 gac ttt cgg atc aat cgt ttc ttc gat aag acc gat atg gag aag cag          144
Asp Phe Arg Ile Asn Arg Phe Phe Asp Lys Thr Asp Met Glu Lys Gln
            35                  40                  45 ctc gaa cac ttg aaa aca ttc atg acc gtc gcg ttt ggc ggg ccc aat          192
Leu Glu His Leu Lys Thr Phe Met Thr Val Ala Phe Gly Gly Pro Asn
 50                  55                  60 aat tac act ggg cgt tcg tta cgg gat ggt cat gcg cgc ttg gtc aag          240
```

-continued

| | | | | | | | | | | | | | | | | |
|---|---|---|---|---|---|---|---|---|---|---|---|---|---|---|---|---|
| Asn | Tyr | Thr | Gly | Arg | Ser | Leu | Arg | Asp | Gly | His | Ala | Arg | Leu | Val | Lys | |
| 65 | | | | 70 | | | | | 75 | | | | | | 80 | |

```
atg ggg ttg aac gac tct cac ttt gat gcg gtt atg ggt cat ttg gga        288
Met Gly Leu Asn Asp Ser His Phe Asp Ala Val Met Gly His Leu Gly
            85                  90                  95 gcg acg atg cag gaa ttg aat gta cct gcg gaa ttg att gcc gaa gcg        336
Ala Thr Met Gln Glu Leu Asn Val Pro Ala Glu Leu Ile Ala Glu Ala
        100                 105                 110 gcg gcg atc gtg gag tcg gtg cgc ggc gag gtc tta gga aag tag            381
Ala Ala Ile Val Glu Ser Val Arg Gly Glu Val Leu Gly Lys
        115                 120                 125
```

<210> SEQ ID NO 4
<211> LENGTH: 126
<212> TYPE: PRT
<213> ORGANISM: Methylomonas sp. 16a

<400> SEQUENCE: 4

Met Ser Glu Glu Gln Lys Val Ser Leu Tyr Glu Arg Ile Gly Gly Glu
1               5                   10                  15

Ala Ala Val Asn Ala Ala Val Asp Leu Phe Tyr Asp Lys Val Leu Asn
            20                  25                  30

Asp Phe Arg Ile Asn Arg Phe Phe Asp Lys Thr Asp Met Glu Lys Gln
        35                  40                  45

Leu Glu His Leu Lys Thr Phe Met Thr Val Ala Phe Gly Gly Pro Asn
    50                  55                  60

Asn Tyr Thr Gly Arg Ser Leu Arg Asp Gly His Ala Arg Leu Val Lys
65                  70                  75                  80

Met Gly Leu Asn Asp Ser His Phe Asp Ala Val Met Gly His Leu Gly
            85                  90                  95

Ala Thr Met Gln Glu Leu Asn Val Pro Ala Glu Leu Ile Ala Glu Ala
        100                 105                 110

Ala Ala Ile Val Glu Ser Val Arg Gly Glu Val Leu Gly Lys
        115                 120                 125

<210> SEQ ID NO 5
<211> LENGTH: 417
<212> TYPE: DNA
<213> ORGANISM: Methylomonas sp. 16a
<220> FEATURE:
<221> NAME/KEY: CDS
<222> LOCATION: (1)..(417)

<400> SEQUENCE: 5 atg tca gca caa acg ccc tat gat ttt ata ggc gga gaa cag gcc att        48
Met Ser Ala Gln Thr Pro Tyr Asp Phe Ile Gly Gly Glu Gln Ala Ile
1               5                   10                  15 cgc agc ctg gtc gac aga ttt tat ttt tac atg gac att ttg ccg gaa        96
Arg Ser Leu Val Asp Arg Phe Tyr Phe Tyr Met Asp Ile Leu Pro Glu
            20                  25                  30 gca caa ggc att cgc gcc atg cat caa ccc aat ctg aac tcg gcc aag        144
Ala Gln Gly Ile Arg Ala Met His Gln Pro Asn Leu Asn Ser Ala Lys
        35                  40                  45 gac aaa ctt ttc aaa ttc ttg tcc ggt tgg ctg gga gga cct aac ctc        192
Asp Lys Leu Phe Lys Phe Leu Ser Gly Trp Leu Gly Gly Pro Asn Leu
    50                  55                  60 tac atc cag gaa ttc ggc cac ccg atg ctg aga atg cgc cac ttc ccg        240
Tyr Ile Gln Glu Phe Gly His Pro Met Leu Arg Met Arg His Phe Pro
65                  70                  75                  80 ttc aaa atc ggc gaa gcc gaa cgc gac caa tgg atg ctg tgc atg aac        288
```

```
Phe Lys Ile Gly Glu Ala Glu Arg Asp Gln Trp Met Leu Cys Met Asn
                85                  90                  95 aaa gcc ctg gcc gaa gtt ccg atg gac ccg cgc ttg cac acc aac atc      336
Lys Ala Leu Ala Glu Val Pro Met Asp Pro Arg Leu His Thr Asn Ile
            100                 105                 110 aca aac gcg ctg caa caa ctg gcc acg cac atg atc aac caa gaa acc      384
Thr Asn Ala Leu Gln Gln Leu Ala Thr His Met Ile Asn Gln Glu Thr
        115                 120                 125 gaa tcg ccg agt acc gca gac gat cga agt tga                          417
Glu Ser Pro Ser Thr Ala Asp Asp Arg Ser
    130                 135
```

<210> SEQ ID NO 6
<211> LENGTH: 138
<212> TYPE: PRT
<213> ORGANISM: Methylomonas sp. 16a

<400> SEQUENCE: 6

```
Met Ser Ala Gln Thr Pro Tyr Asp Phe Ile Gly Glu Gln Ala Ile
1               5                   10                  15

Arg Ser Leu Val Asp Arg Phe Tyr Phe Tyr Met Asp Ile Leu Pro Glu
            20                  25                  30

Ala Gln Gly Ile Arg Ala Met His Gln Pro Asn Leu Asn Ser Ala Lys
        35                  40                  45

Asp Lys Leu Phe Lys Phe Leu Ser Gly Trp Leu Gly Gly Pro Asn Leu
    50                  55                  60

Tyr Ile Gln Glu Phe Gly His Pro Met Leu Arg Met Arg His Phe Pro
65                  70                  75                  80

Phe Lys Ile Gly Glu Ala Glu Arg Asp Gln Trp Met Leu Cys Met Asn
                85                  90                  95

Lys Ala Leu Ala Glu Val Pro Met Asp Pro Arg Leu His Thr Asn Ile
            100                 105                 110

Thr Asn Ala Leu Gln Gln Leu Ala Thr His Met Ile Asn Gln Glu Thr
        115                 120                 125

Glu Ser Pro Ser Thr Ala Asp Asp Arg Ser
    130                 135
```

<210> SEQ ID NO 7
<211> LENGTH: 264
<212> TYPE: DNA
<213> ORGANISM: Methylomonas sp. 16a

<400> SEQUENCE: 7

```
taaggattgg ggtgcgtcgc cggtcgcggc ggcgctcctc gacggcagag ttggtgccag     60
gttggcggat gattgatgcc gaatattacg cgaccaattc tcgaggcaaa tgaactgtga    120
gctactgagt tgcaggcatt gacagccatc ccatttctat catacagtta cggacgcatc    180
acgagtaggt gataagccta gcagattgcg gcagttggca aaatcagcta ttactaataa    240
ttaaaaactt tcggagcaca tcac                                           264
```

<210> SEQ ID NO 8
<211> LENGTH: 29
<212> TYPE: DNA
<213> ORGANISM: Artificial sequence
<220> FEATURE:
<223> OTHER INFORMATION: Primer

<400> SEQUENCE: 8

```
ccatgggcta gctaaggatt ggggtgcgt                                       29
```

<210> SEQ ID NO 9
<211> LENGTH: 30
<212> TYPE: DNA
<213> ORGANISM: Artificial sequence
<220> FEATURE:
<223> OTHER INFORMATION: Primer

<400> SEQUENCE: 9
ccatggacta gtgtgatgtg ctccgaaagt                                   30

<210> SEQ ID NO 10
<211> LENGTH: 34
<212> TYPE: DNA
<213> ORGANISM: Artificial sequence
<220> FEATURE:
<223> OTHER INFORMATION: Primer

<400> SEQUENCE: 10
actagtacaa gcagaggaaa atcattatga gtgc                              34

<210> SEQ ID NO 11
<211> LENGTH: 27
<212> TYPE: DNA
<213> ORGANISM: Artificial sequence
<220> FEATURE:
<223> OTHER INFORMATION: Primer

<400> SEQUENCE: 11
actagttagc gacccaatac gtcggtg                                      27

<210> SEQ ID NO 12
<211> LENGTH: 31
<212> TYPE: DNA
<213> ORGANISM: Artificial sequence
<220> FEATURE:
<223> OTHER INFORMATION: Primer

<400> SEQUENCE: 12
actagtaact atgaggatgc tatgagcgaa g                                 31

<210> SEQ ID NO 13
<211> LENGTH: 26
<212> TYPE: DNA
<213> ORGANISM: Artificial sequence
<220> FEATURE:
<223> OTHER INFORMATION: Primer

<400> SEQUENCE: 13
actagtctac tttcctaaga cctcgc                                       26

<210> SEQ ID NO 14
<211> LENGTH: 43
<212> TYPE: DNA
<213> ORGANISM: Artificial sequence
<220> FEATURE:
<223> OTHER INFORMATION: Primer

<400> SEQUENCE: 14
actagtaagg aggaataaac catgtcagca caaacgccct atg                    43

<210> SEQ ID NO 15
<211> LENGTH: 28
<212> TYPE: DNA
<213> ORGANISM: Artificial sequence
<220> FEATURE:

-continued

<223> OTHER INFORMATION: Primer

<400> SEQUENCE: 15
actagtcaac ttcgatcgtc tgcggtac                                              28

<210> SEQ ID NO 16
<211> LENGTH: 56
<212> TYPE: DNA
<213> ORGANISM: Artificial sequence
<220> FEATURE:
<223> OTHER INFORMATION: Primer

<400> SEQUENCE: 16
ggccatgcca attgactaga aaggaggaat aaaccatgac cgtcgatcac gacgca         56

<210> SEQ ID NO 17
<211> LENGTH: 42
<212> TYPE: DNA
<213> ORGANISM: Artificial sequence
<220> FEATURE:
<223> OTHER INFORMATION: Primer

<400> SEQUENCE: 17
cgcgtacgcc taggtcaggc gccgttgctg gatgagccgc gt                              42

<210> SEQ ID NO 18
<211> LENGTH: 11107
<212> TYPE: DNA
<213> ORGANISM: artificial sequence
<220> FEATURE:
<223> OTHER INFORMATION: Plasmid pDCQ343

<400> SEQUENCE: 18
accttcggga gcgcctgaag cccgttctgg acgccctggg gccgttgaat cgggatatgc        60
aggccaaggc cgccgcgatc atcaaggccg tgggcgaaaa gctgctgacg gaacagcggg       120
aagtccagcg ccagaaacag gcccagcgcc agcaggaacg cgggcgcgca catttccccg       180
aaaagtgcca cctgacgtct aagaaaccat tattatcatg acattaacct ataaaaatag       240
gcgtatcacg aggccctttg cgccgaataa atacctgtga cggaagatca cttcgcagaa       300
taaataaatc ctggtgtccc tgttgatacc gggaagccct gggccaactt ttggcgaaaa       360
tgagacgttg atcggcacgt aagaggttcc aactttcacc ataatgaaat aagatcacta       420
ccgggcgtat tttttgagtt atcgagattt tcaggagcta aggaagctaa aatggagaaa       480
aaaatcactg gatataccac cgttgatata tcccaatggc atcgtaaaga acattttgag       540
gcatttcagt cagttgctca atgtacctat aaccagaccg ttcagctgga tattacggcc       600
tttttaaaga ccgtaaagaa aaataagcac aagttttatc cggcctttat tcacattctt       660
gcccgcctga tgaatgctca tccggaattc actagaaagg aggaataaac catgaccgtc       720
gatcacgacg cacggatcag cctgctgctg ccgcagccat cggcgccgc gtggctggcg       780 atccatgtcg ggcgatcgt gtggtggcga tggagcccgg cgacggcggt gctcgcgatc       840
cccgtcgtgc tcgtacaggc gtggctgagc accggcctgt tcatcgtcgc gcacgattgc       900
atgcacggat cgttcgtgcc cggccggccc gcggtcaacc ggaccgtcgg gacgctgtgc       960
ctcggcgcct atgcgggact gtcctatggc cagctccatc ccaagcatca tgcgcatcac      1020
gatgcgccgg gcaccgccgc cgaccccgat ttccatgccg gcgcgccgcg atccgcactg      1080 ccgtggtttcg cgcgcttctt caccagctat tacacgcacg ccagatcct ccggatcacc      1140 gcggcggcgg tgctgtacat gctgctcggt gtgtcgctgc tcaacatcgt cgtgttctgg      1200

```
gcgttgccgg cgctgatcgc gctggcgcag ctgttcgtct tcggcaccttc cctgccgcat    1260
cgccacggcg acacgccgtt cgcggacgcg cacaatgccc gcagcaacgg ctggccacgg    1320
ctggcgtcgc tggcgacctg cttccacttc ggcgcctatc atcacgaaca tcacctgagc    1380
ccgtggacgc cctggtggca gttgccgcgc gtcggccagc ctgccgccgg acaccggtcg    1440
ttaagcaaag accggtagac tagaaaggag gaataaaacca tgtcctggcc gacgatgatc    1500
ctgctgttcc tcgccaccttc cctggggatg gaggtcttcg cctgggcgat gcatcgctat    1560
gtcatgcacg gcctgctgtg gacctggcac cgcagccatc atgagccgca cgacgacgtg    1620
ctggaaagga acgacctgtt cgcggtggtg ttcgccgccc cggccatcat cctcgtcgcc    1680
ttgggtctac atctgtggcc ttggatgctg ccgatcggcc tgggcgttac ggcctatgga    1740
ctggtttatt tcttctttca cgacgggctg gtgcatcgcc ggttcccgac agggatcgca    1800
gggcgctcgg cgttctggac gcgacgcatt caggcccacc ggctgcatca cgcggtgcgg    1860
acacgcgagg gctgcgtatc gttcggcttc ctttgggtgc ggtcggcgcg cgcgctgaag    1920
gccgaactgt ctcagaaacg cggctcatcc agcaacggcg cctgaactag taccaaccat    1980
ggatagccat tatgaccacc catgtcgaca ccacagcaca tcagacaagc gaactccttc    2040
agctgcagca aattttacag gcgcatcttg aacatttact gcctgccgga cagcaaagcg    2100
atcgcgtgcg tgccgcgatg cgtgccggaa cgctggcgca gggcaaacgt attcgtcctt    2160
tattactgct gctggcagcg cgcgatatgg gttgcgagct gacgcaaaat ggcgttctcg    2220
atctcgcctg tgcagtggaa atggtgcacg cggcatcgct gattctggat gacattccct    2280
cgatggataa cgcgcagatg cgtcgtggtc gccctaccgt gcatcgcgaa tttggtgaaa    2340
acgtggcgat tctcgccgcc atcgcgctgc ttagccgcgc atttgaagtg attgccattg    2400
cacccggttt gcctgccata cataaatctg aagcgattgc tgaactctcc gctgccgtcg    2460
gcctgcaggg cttagtgcaa gggcaattcc aggatctgca cgacggcacg cagagccgca    2520
gcccggaagc gatcgccatg accaacgaac tgaaaaccag cgtgctgttt cgcgccacgc    2580
tgcaaatggc ggcgattgcc gctgacgctt caccgcaggt gcggcaaaga cttagcttct    2640
tcgcccagga tttgggccag gcgtttcaac tgctcgacga cctcgccgac ggttgcaaac    2700
acaccggtaa agatgtgcac caggatcagg gcaaatccac gctggtacag atgctcggtg    2760
ctgacggcgc ggaacgtcgc ctgcgcgatc acctgcgcag cgcagatgca caccttgcct    2820
gcgcctgcca tcgcggcatc gccactcgcc aatatatgca cgcgctgttt aatcaacagc    2880
tagcgatatt caactgaaag tcgtgctggc ggaggcgacc tgatgcgcac gcaatacgat    2940
gtgattttgg tcggtgctgg actggcgaat ggcttgattg cgctgcgtct gcgtcaattg    3000
cagccacaac tgaaatgcct gttgctggag agcgatgcgc atccggcagg caatcatacc    3060
tggtcgtttc atcacagcga tctcagcgcc gaacaacttc gctggctgca accgctgatt    3120
accgtgcgtt ggtcaggtta tcaggtgcgt tttcctgcgc tgcgccgcaa tctggacggg    3180
gattattgtt ccatcgcatc aggcgatttt gcccgccatc tttacgcggc gatgggtgac    3240
gatctgtgga caaacacagc cgtacaacag gtaaaaccca cgcaggtgac gctggcggat    3300
ggccgtgaac ttgctgcgca agtggtgatt gatggtcgcg gcctgcagcc gacgccacat    3360
ctgcagctgg gttatcaggt gtttcttgga caagagtgga gctggcgcag ccgcacggc    3420
ctgcagcagc cgatcctgat ggatgccacc gtcgatcagc aagcgggtta tcgttttgtc    3480
tacacgctgc cgctcagcgc cgatcggcta ttgattgaag atacccatta cgttaaccag    3540
```

-continued

```
cccgcgctgg cggagaacac cgctcgtcag cacatcgccg actatgccaa tcagcaaggc    3600
tggacgctga gtacgctgct gcgtgaagag cacggcatat taccgattac cctgagcggc    3660
aacatcgatc gattctggca acagcagcgc ggccaagcgt gcagcggcct gcgcgccggg    3720
ctgtttcatg ccaccaccgg ttactccttg ccgtccgccg tggcgctagc ggagttggta    3780
gcagcgctgt tgcccaccga tgccctcacg ctcagccaac atatcgaacg ctttgcccgt    3840
cagcagtggc gcgaacagcg attttttccgt ctgctaaacc gcatgctgtt tttgccggtt    3900
aagccgcagc agcgctggcg cgtgatgcaa cgttttttacc ggctcgatgc cgggttaatt    3960
agccgctttt acgccgggca actgcgcctg cgcgataaaa cgcggattct gtgcggcaag    4020
ccgccggtgc ccatcggtga agcgctgcgc gcgctgttga actctgtcga accagggaag    4080
aaaaaatgaa acgcacttat gtgattggcg caggctttgg cggcctggcg ctggcgattc    4140
gcctgcaagc ggcgggcata ccaaccaccct tactcgagca gcgcgacaaa ccgggcggac    4200
gcgcctatgt gtttgaggac agtggcttta ccttcgatgc cggacccacg gtgatcaccg    4260
atcccagcgc catcgaagag ttgttcacgc tggcaggaaa atcgctcagc gattacgtcg    4320
agctgatgcc ggtaacgccc ttctatcgcc tgtgctggga agatggcaaa cagcttgatt    4380
acgacaataa tcagccgctg ctggagcagc agatcgccac gttcaatccg caagatgtag    4440
aaggctatcg tcaatttctt gcctattcac gtgaagtatt tagagagggt tatctgaaac    4500
tcggcacggt gccgtttctg caggtgcgtg acatgctgcg cgtcgcgccg cagttgggac    4560
gtctgcaagc atggcgcagc gtctacagca tggtggcgaa atttattcag gacgatcatc    4620
tgcgtcaggc gttttccttc cactcattgc tggtgggcgg taatccttt gcaacgtcat    4680
cgatctatac cttaattcat gcgctggagc gtgaatgggg cgtgtggttt ccgcgcggcg    4740
gcaccggcgc gctggtgcag ggcatggcgc gactgttcga ggacttgggc ggcgagctgt    4800
tactgaatgc cgaagtgagc cagctggaaa ccagcggcaa tcgcattagc ggcgttcagt    4860
tagagggcgg acgacgcttc gatgccgccg ctgtggcctc caatgccgac gtggtgcata    4920
cctacgacaa actgcttcgc caccatccgc tggcaatgaa acgtgcgaca tcgctgaagc    4980
gtaagcgcat gagcaactcg ctgtttgtac tctattttgg cctgaatcag ccgcatgaac    5040
agctcgcgca ccacaccgtc tgttttggcc cgcgttatcg tgagttgatc gatgagattt    5100
tcaacagcag ccagctggca gacgattttt cactttacct gcacgcgccc tgcagcagcg    5160
atccgtcgct ggcaccgccc ggctgcggca gcttttatgt gttagcgccg gtgccgcatc    5220
tcggcaccgc tgacatcgac tggcaacagg aaggaccgcg cttgcgcgat cgaattttg    5280
cttatctgga gcagcactac atgccgggat tacgtcagca attagtgaca cacagaatgt    5340
ttacgccgtt tgattttcgc gacacgctgc atgcccatca cggctcggcg ttttcgctgg    5400
agccgatttt gacgcaaagc gcctggttcc gcccgcataa ccgcgatgcc gatatcagca    5460
atctctatct ggtgggtgcc ggtacgcatc caggcgcggg cgtgcccggc gtgatcggtt    5520
cggccaaggc caccgccagg ctgatgctgg aggatcgcgc cgaatgaatc gacagccttt    5580
acttgagcaa gtaacgcaaa ccatggcggt gggctcgaag agtttcgcca ccgccgccaa    5640
gctgtttgat gcaccgacgc gccgcagcac gctgatgctg tatgcgtggt gtcgtcactg    5700
cgatgatgtg attgatggc aaacgctggg cgaaggcggc acgcagcatg ccgtcgaaga    5760
cgcgcaggca cgtatgcagc atctgcaaat tgaaacccgc cgcgcctaca gcggcgcgca    5820
catggatgaa ccggcgttta gggcgtttca ggaagtggcg atcattcacc agctgccgca    5880
acaactggcg tttgatcatc tggaaggctt cgctatggat gcacgcaacg aacattacgc    5940
```

```
gagcttcgat gacacgctgc gttactgcta tcacgtcgcg ggcgtggtcg gtttgatgat    6000
ggcgcgcgta atgggcgtgc gcgacgaagc ggtgctcgat cacgcctgcg atttaggact    6060
ggcgttccag ctcactaaca ttgcgcgcga cattgtagaa gatgccgaaa atggtcgctg    6120
ctatctgccg caatcctggc tcgatcaggc gggattacgc gccgatacgc tgactgcacc    6180
gcaacatcgt gcagcgctcg cctcactggc agcgcgttta gtggcggagg cggaacccta    6240
ttatcactcg gcgcgatccg gtttaccggg tttaccgctg cgctcggcgt gggccatcgc    6300
tacggctcgc ggcgtttatc gcgaaattgg cgtcaaagtt cagcacgccg gtgtgcacgc    6360
ctgggattca cggcagcgca ccagtaaagg tgaaaaactg gcgctgctgg tgaaaggggc    6420
aggtttggcg atcacttcgc gtgtgtctcg tcctgaaccg cgtccggctg gtctgtggca    6480
gcgtcctcgt tgaattccgt atggcaatga agacggtga gctggtgata tgggatagtg    6540
ttcacccttg ttacaccgtt ttccatgagc aaactgaaac gttttcatcg ctctggagtg    6600
aataccacga cgatttccgg cagtttctac acatatattc gcaagatgtg gcgtgttacg    6660
gtgaaaacct ggcctatttc cctaaagggt ttattgagaa tatgttttc gtctcagcca    6720 atccctgggt gagtttcacc agttttgatt taaacgtggc caatatggac aacttcttcg    6780
cccccgtttt caccatgggc aaatattata cgcaaggcga caaggtgctg atgccgctgg    6840
cgattcaggt tcatcatgcc gtctgtgatg gcttccatgt cggcagaatg cttaatgaat    6900
tacaacagta ctgcgatgag tggcagggcg gggcgtaatt ttttaaggc agttattggt    6960 gcccttaaac gcctggtgct acgcctgaat aagtataata gcggatgaa tggcagaaat    7020 tcgaaagcaa attcgacccg gtcgtcggtt cagggcaggg tcgttaaata gccgcttatg    7080
tctattgctg gtttaccggt ttattgacta ccggaagcag tgtgaccgtg tgcttctcaa    7140
atgcctgagg ccagtttgct caggctctcc ccgtggaggt aataattgac gatatgatca    7200
tttattctgc ctcccagagc ctgataaaaa cggtgaatcc gttagcgagg tgccgccggc    7260
ttccattcag gtcgaggtgg cccggctcca tgcaccgcga cgcaacgcgg ggaggcagac    7320
aaggtatagg gcggcgaggc ggctacagcc gatagtctgg aacagcgcac ttacgggttg    7380
ctgcgcaacc caagtgctac cggcgcggca gcgtgacccg tgtcggcggc tccaacggct    7440
cgccatcgtc cagaaaacac ggctcatcgg gcatcggcag gcgctgctgc ccgcgccgtt    7500
cccattcctc cgtttcggtc aaggctggca ggtctggttc catgcccgga atgccgggct    7560
ggctgggcgg ctcctcgccg gggccggtcg gtagttgctg ctcgcccgga tacagggtcg    7620
ggatgcggcg caggtcgcca tgccccaaca gcgattcgtc ctggtcgtcg tgatcaacca    7680
ccacggcgga actgaacacc gacaggcgca actggtcgcg gggctggccc cacgccacgc    7740
ggtcattgac cacgtaggcc gacacggtgc cggggccgtt gagcttcacg acggagatcc    7800
agcgctcggc caccaagtcc ttgactgcgt attggaccgt ccgcaaagaa cgtccgatga    7860
gcttggaaag tgtcttctgg ctgaccacca cggcgttctg gtgcccatc tgcgccacga    7920 ggtgatgcag cagcattgcc gccgtgggtt cctcgcaat aagcccggcc cacgcctcat    7980
gcgctttgcg ttccgtttgc acccagtgac cgggcttgtt cttggcttga atgccgattt    8040
ctctggactg cgtggccatg cttatctcca tgcggtaggg tgccgcacgg ttgcggcacc    8100
atgcgcaatc agctgcaact tttcggcagc gcgacaacaa ttatgcgttg cgtaaaagtg    8160
gcagtcaatt acagatttc tttaacctac gcaatgagct attgcggggg gtgccgcaat    8220
gagctgttgc gtaccccct tttttaagtt gttgatttt aagtctttcg catttcgccc    8280
```

-continued

```
tatatctagt tctttggtgc ccaaagaagg gcacccctgc ggggttcccc cacgccttcg    8340
gcgcggctcc ccctccggca aaaagtggcc cctccggggc ttgttgatcg actgcgcggc    8400
cttcggcctt gcccaaggtg gcgctgcccc cttggaaccc ccgcactcgc cgccgtgagg    8460
ctcgggacct gcagggggggg gggggaaagc cacgttgtgt ctcaaaatct ctgatgttac    8520
attgcacaag ataaaaatat atcatcatga acaataaaac tgtctgctta cataaacagt    8580
aatacaaggg gtgttatgag ccatattcaa cgggaaacgt cttgctcgag gccgcgatta    8640
aattccaaca tggatgctga tttatatggg tataaatggg ctcgcgataa tgtcgggcaa    8700
tcaggtgcga caatctatcg attgtatggg aagcccgatg cgccagagtt gtttctgaaa    8760
catggcaaag gtagcgttgc caatgatgtt acagatgaga tggtcagact aaactggctg    8820
acggaattta tgcctcttcc gaccatcaag catttttatcc gtactcctga tgatgcatgg    8880
ttactcacca ctgcgatccc cgggaaaaca gcattccagg tattagaaga atatcctgat    8940
tcaggtgaaa atattgttga tgcgctggca gtgttcctgc gccggttgca ttcgattcct    9000
gtttgtaatt gtccttttaa cagcgatcgc gtatttcgtc tcgctcaggc gcaatcacga    9060
atgaataacg gtttggttga tgcgagtgat tttgatgacg agcgtaatgg ctggcctgtt    9120
gaacaagtct ggaaagaaat gcataagctt ttgccattct caccggattc agtcgtcact    9180
catggtgatt tctcacttga taaccttatt tttgacgagg ggaaattaat aggttgtatt    9240
gatgttggac gagtcggaat cgcagaccga taccaggatc ttgccatcct atggaactgc    9300
ctcggtgagt tttctccttc attacagaaa cggctttttc aaaaatatgg tattgataat    9360
cctgatatga ataaattgca gtttcatttg atgctcgatg agttttttcta atcagaattg    9420
gttaattggt tgtaacactg gcagagcatt acgctgactt gacgggacgg cggctttgtt    9480
gaataaatcg aacttttgct gagttgaagg atcagatcac gcatcttccc gacaacgcag    9540
accgttccgt ggcaaagcaa aagttcaaaa tcaccaactg gtccacctac aacaaagctc    9600
tcatcaaccg tggctccctc actttctggc tggatgatgg ggcgattcag gcctggtatg    9660
agtcagcaac accttcttca cgaggcagac ctcagcgccc ccccccccct gcaggtctcg    9720
gggggcaggc gggcgggctt cgccttcgac tgccccact cgcataggct tgggtcgttc    9780
caggcgcgtc aaggccaagc cgctgcgcgg tcgctgcgcg agccttgacc cgccttccac    9840
ttggtgtcca accggcaagc gaagcgcgca ggccgcaggc cggaggcttt tccccagaga    9900
aaattaaaaa aattgatggg gcaaggccgc aggccgcgca gttggagccg gtgggtatgt    9960
ggtcgaaggc tgggtagccg gtgggcaatc cctgtggtca agctcgtggg caggcgcagc   10020
ctgtccatca gcttgtccag cagggttgtc cacgggccga gcgaagcgag ccagccggtg   10080
gccgctcgcg gccatcgtcc acatatccac gggctggcaa gggagcgcag cgaccgcgca   10140
gggcgaagcc cggagagcaa gcccgtaggg cgccgcagcc gccgtaggcg gtcacgactt   10200
tgcgaagcaa agtctagtga gtatactcaa gcattgagtg gcccgccgga ggcaccgcct   10260
tgcgctgccc ccgtcgagcc ggttggacac caaagggag gggcaggcat ggcggcatac   10320
gcgatcatgc gatgcaagaa gctggcgaaa atgggcaacg tggcggccag tctcaagcac   10380
gcctaccgcg agcgcgagac gcccaacgct gacgccagca ggacgccaga aacgagcac   10440
tgggcggcca gcagcaccga tgaagcgatg gccgactgc gcgagttgct gccagagaag   10500
cggcgcaagg acgctgtgtt ggcggtcgag tacgtcatga cggccagccc ggaatggtgg   10560
aagtcggcca gccaagaaca gcaggcggcg ttcttcgaga aggcgcacaa gtggctggcg   10620
gacaagtacg gggcggatcg catcgtgacg gccagcatcc accgtgacga aaccagcccg   10680
```

-continued

```
cacatgaccg cgttcgtggt gccgctgacg caggacggca ggctgtcggc caaggagttc    10740
atcggcaaca aagcgcagat gacccgcgac cagaccacgt ttgcggccgc tgtggccgat    10800
ctagggctgc aacggggcat cgagggcagc aaggcacgtc acacgcgcat tcaggcgttc    10860
tacgaggccc tggagcggcc accagtgggc cacgtcacca tcagcccgca agcggtcgag    10920
ccacgcgcct atgcaccgca gggattggcc gaaaagctgg gaatctcaaa gcgcgttgag    10980
acgccggaag ccgtggccga ccggctgaca aaagcggttc ggcaggggta tgagcctgcc    11040
ctacaggccg ccgcaggagc gcgtgagatg cgcaagaagg ccgatcaagc ccaagagacg    11100
gcccgag                                                              11107
```

<210> SEQ ID NO 19
<211> LENGTH: 51
<212> TYPE: DNA
<213> ORGANISM: Artificial sequence
<220> FEATURE:
<223> OTHER INFORMATION: Primer

<400> SEQUENCE: 19

```
ccatgcgaat tcactagaaa ggaggaataa accatgtcct ggccgacgat g              51
```

<210> SEQ ID NO 20
<211> LENGTH: 38
<212> TYPE: DNA
<213> ORGANISM: Artificial sequence
<220> FEATURE:
<223> OTHER INFORMATION: Primer

<400> SEQUENCE: 20

```
gactgaattc tcaggcgccg ttgctggatg agccgcgt                              38
```

<210> SEQ ID NO 21
<211> LENGTH: 747
<212> TYPE: DNA
<213> ORGANISM: Sphingomonas melonis DC18

<400> SEQUENCE: 21

```
atgaccgtcg atcacgacgc acggatcagc ctgctgctgg ccgcagccat cggcgccgcg     60
tggctggcga tccatgtcgg ggcgatcgtg tggtggcgat ggagcccggc gacggcggtg    120
ctcgcgatcc ccgtcgtgct cgtacaggcg tggctgagca ccggcctgtt catcgtcgcg    180
cacgattgca tgcacggatc gttcgtgccc ggcggcccg cggtcaaccg gaccgtcggg    240
acgctgtgcc tcggcgccta tgcgggactg tcctatggcc agctccatcc caagcatcat    300
gcgcatcacg atgcgccggg caccgccgcc gaccccgatt ccatgccgg cgcgccgcga    360 tccgcactgc cgtggttcgc gcgcttcttc accagctatt acacgcacgg ccagatcctc    420
cggatcaccg cggcggcggt gctgtacatg ctgctcggtg tgtcgctgct caacatcgtc    480
gtgttctggg cgttgccggc gctgatcgcg ctggcgcagc tgttcgtctt cggcaccttc    540
ctgccgcatc gccacggcga cacgccgttc gcggacgcgc acaatgcccg cagcaacggc    600
tggccacggc tggcgtcgct ggcgacctgc ttccacttcg gcgcctatca tcacgaacat    660
cacctgagcc cgtggacgcc ctggtggcag ttgccgcgcg tcggccagcc tgccgccgga    720
caccggtcgt taagcaaaga ccggtag                                         747
```

<210> SEQ ID NO 22
<211> LENGTH: 531
<212> TYPE: DNA

<213> ORGANISM: Novosphingobium aromaticivorans ATCC 700278

<400> SEQUENCE: 22

```
atgggcgggg ccatgcagac gcttgccgcg atcctcattg tcctgggcac ggtcctcgcg      60
atggaattcg tcgcgtggtc gagccacaag tacatcatgc acggcttcgg ctggggctgg     120
caccgcgacc atcatgagcc gcacgaaggg tttctcgaga agaacgatct ctacgccatt     180
gtcggcgcgg cgctttcgat cctgatgttc gcgctgggca gcccgatgat catgggcgcg     240
gatgcctggt ggccgggcac gtggatcggc ctgggcgtcc tgttctatgg cgtgatctat     300
acgctggtgc atgacgggct ggtccaccag cgctggttcc gatgggtccc gaagcgcggc     360
tatgccaagc ggctggtcca ggcgcacaag cttcaccacg ccacgatcgg caaggaaggc     420
ggcgtcagtt tcggcttcgt cttcgcgcgc gaccctgcgg tgctgaagca ggaactgcgg     480
gcccagcgcg aggcaggcat cgccgttctg cgcgaggcag tggacggcta g             531
```

<210> SEQ ID NO 23
<211> LENGTH: 486
<212> TYPE: DNA
<213> ORGANISM: Brevundimonas vesicularis DC263

<400> SEQUENCE: 23

```
atgtcctggc cgacgatgat cctgctgttc ctcgccacct tcctggggat ggaggtcttc      60
gcctgggcga tgcatcgcta tgtcatgcac ggcctgctgt ggacctggca ccgcagccat     120
catgagccgc acgacgacgt gctggaaagg aacgacctgt tcgcggtggt gttcgccgcc     180
ccggccatca tcctcgtcgc cttgggtcta catctgtggc cttggatgct gccgatcggc     240
ctgggcgtta cggcctatgg actggtttat ttcttctttc acgacgggct ggtgcatcgc     300
cggttcccga cagggatcgc agggcgctcg gcgttctgga cgcgacgcat tcaggcccac     360
cggctgcatc acgcggtgcg gacacgcgag ggctgcgtat cgttcggctt cctttgggtg     420
cggtcggcgc gcgcgctgaa ggccgaactg tctcagaaac gcggctcatc cagcaacggc     480
gcctga                                                                486
```

<210> SEQ ID NO 24
<211> LENGTH: 1429
<212> TYPE: DNA
<213> ORGANISM: Methylomonas sp. 16a

<400> SEQUENCE: 24

```
cggtatgctt aacacatgca agtcgaacgc tgaagggtgc ttgcacctgg atgagtggcg      60
gacgggtgag taatgcatag gaatctgcct attagtgggg gataacgtgg ggaaactcac     120
gctaataccg catacgctct acggaggaaa gccgggaccc ttcgggcctg cgctaatag     180
atgagcctat gtcggattag ctagttggtg gggtaaaggc ctaccaaggc gacgatccgt     240
agctggtctg agaggatgat cagccacact gggactgaga cacggcccag actcctacgg     300
gaggcagcag tggggaatat tggacaatgg gcgcaagcct gatccagcaa taccgcgtgt     360
gtgaagaagg cctgagggtt gtaaagcact tcaatggga aggaacacct atcggttaat     420
acccggtaga ctgacattac ccatacaaga agcaccggct aactccgtgc cagcagccgc     480
ggtaatacgg agggtgcaag cgttaatcgg aattactggg cgtaaagcgt gcgtaggcgg     540
ttttttaagt cagatgtgaa agccctgggc ttaacctggg aactgcattt gatactgggg     600
aactagagtt gagtagagga gagtggaatt tcaggtgtag cggtgaaatg cgtagagatc     660
tgaaggaaca ccagtggcga aggcggctct ctggactcaa actgacgctg aggtacgaaa     720
```

```
gcgtgggtag caaacaggat tagatacct ggtagtccac gccgtaaacg atgtcaacta       780
accgttgggt tcttaaagaa cttagtggtg gagctaacgt attaagttga ccgcctgggg       840
agtacggccg caaggctaaa actcaaatga attgacgggg gcccgcacaa gcggtggagc       900
atgtggttta attcgatgca acgcgaagaa ccttacctac ccttgacatc ctcggaactt       960
gtcagagatg acttggtgcc ttcgggaacc gagagacagg tgctgcatgg ctgtcgtcag      1020
ctcgtgtcgt gagatgttgg gttaagtccc gtaacgagcg caaccctat ccttagttgc       1080 cagcgcgtca tggcgggaac tctagggaga ctgccggtga taaaccggag gaaggtgggg      1140
acgacgtcaa gtcatcatgg cccttatggg tagggctaca cacgtgctac aatggtcggt      1200
acagagggtt gcgaactcgc gagagccagc caatcccaaa aagccgatcc tagtccggat      1260
tgcagtctgc aactcgactt gcatgaagtc ggaatcgcta gtaatcgcgg atcagaatgc      1320
cgcggtgaat acgttcccgg gccttgtaca caccgcccgt cacaccatgg gagtgggttg      1380
caaaagaagt aggtagttta accttcggga gggcgcttac cactttgtg                  1429
```

BACTERIAL HEMOGLOBIN GENES AND THEIR USE TO INCREASE CAROTENOID PRODUCTION

This application claims the benefit of U.S. Provisional Application No. 60/671,449 filed Apr. 14, 2005.

FIELD OF THE INVENTION

This invention is in the field of microbiology and molecular biology. More specifically, this invention pertains to nucleic acid molecules that encode oxygen-binding proteins and their use in improving carotenoid production.

BACKGROUND OF THE INVENTION

Carotenoids are pigments that are ubiquitous throughout nature and synthesized by all photosynthetic organisms and in some heterotrophic bacteria and fungi. Carotenoids provide color for flowers, vegetables, insects, fish and birds. Colors of carotenoid range from yellow to red with variations of brown and purple. As precursors of vitamin A, carotenoids are fundamental components in the human diet and play an important role in human health. Animals are unable to synthesize carotenoids de novo and must obtain them through diet. Manipulation of carotenoid composition and production in plants or bacteria can provide new and/or improved sources of carotenoids. Industrial uses of carotenoids include, among others, pharmaceuticals, food supplements, animal feed additives, and colorants in cosmetics.

The genetics of carotenoid biosynthesis are well known (Armstrong, G., in *Comprehensive Natural Products Chemistry*, Elsevier Press, volume 2, pp 321–352 (1999)); Lee, P. and Schmidt-Dannert, C., *Appl Microbiol Biotechnol*, 60:1–11 (2002); Lee et al., *Chem Biol* 10:453–462 (2003), and Fraser, P. and Bramley, P. (*Progress in Lipid Research*, 43:228–265 (2004)). This pathway is extremely well studied in the Gram-negative, pigmented bacteria of the genera *Pantoea*, formerly known as *Erwinia*. Of particular interest are the genes responsible for the production of $C_{40}$ carotenoids used as pigments in animal feed (e.g., canthaxanthin and astaxanthin).

The genes associated with carotenoid biosynthesis ($C_{40}$) can be generally divided into two categories of genes: 1) the $C_{40}$ carotenoid backbone biosynthesis genes responsible for the elongation, desaturation, and cyclization steps necessary for the synthesis of the 40-carbon backbone (i.e., the crtE, crtB, crtI, and crtY genes responsible for the biosynthesis of β-carotene) and 2) subsequent carotenoid modification genes (i.e., crtW, crtO, crtZ, etc.), which introduce various functional groups (e.g., keto groups and hydroxyl groups) to the 40-carbon backbone. The biosynthesis of ketocarotenoids and hydroxylated carotenoids is of particular interest as they are commercially important pigments (e.g., canthaxanthin, astaxanthin, zeaxanthin, etc.) used in a variety of applications, including the animal feed market. Recombinant expression of the genes involved in carotenoid production has been reported in a variety of hosts.

Ketocarotenoid biosynthesis typically requires expression of a carotenoid ketolase. Two classes of carotenoid ketolase have been reported (CrtW/bkt and CrtO). The two classes have similar functionality yet appear to have arisen independently as they share very little sequence similarity (U.S. Pat. No. 6,984,523 and U.S. Ser. No. 11/015,433, each incorporated herein by reference). Carotenoid ketolases introduce keto groups to the ionone ring of cyclic carotenoids forming ketocarotenoids including, but not limited to echinenone, 3-hydroxyechinenone, 3'-hydroxyechinenone, adonixanthin, adonirubin, canthaxanthin and astaxanthin.

Biosynthesis of hydroxylated carotenoids typically requires expression of a carotenoid hydroxylase. Carotenoid hydroxylases introduce hydroxyl groups to the ionone ring of the cyclic carotenoids, such as β-carotene or canthaxanthin. Bacterial biosynthesis of astaxanthin requires functional expression of both a carotenoid ketolase and a CrtZ carotenoid hydroxylase, which is encoded by a crtZ gene as reported in U.S. Ser. No. 11/200,394, incorporated herein by reference. Besides astaxanthin, examples of hydroxylated carotenoids include β-cryptoxanthin, zeaxanthin, 3-hydroxyechinenone, 3'-hydroxyechinenone, adonirubin, adonixanthin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal, and lutein.

It has been reported for microbial carotenoid production that the concentration of dissolved oxygen within a microbial culture affects the carotenoid production profile (U.S. Pat. No. 6,825,002 to Tsubokura et al.). This is because both carotenoid ketolases and carotenoid hydroxylases require molecular oxygen to synthesize canthaxanthin and astaxanthin. Conversion of β-carotene to canthaxanthin and/or astaxanthin, as well as various intermediates in the pathway, can be adversely affected under oxygen limited conditions.

A problem in large-scale fermentation is that increasing dissolved oxygen mechanistically is costly and often not workable. A biological method is therefore needed to increase the overall availability of cellular oxygen, that is, to increase internal $O_2$ tension within a recombinant microbial cell. One way to do this is to increase the cellular components that aid in the intracellular storage and delivery of oxygen. It has been reported that bacterial hemoglobins, a subset of the larger hemoglobin-like superfamily, perform these functions (Frey, A. D. and Kallio, P. T., *FEMS Microbiol Rev.* 27:525–545 (2003)). Three different types of bacterial hemoglobins have been identified: 1) the *Vitreoscilla* hemoglobin (VHb), 2) the flavohemoglobins (FHb), and 3) the truncated hemoglobins (trHb). The truncated hemoglobins are further divided into 3 groups, Group I (HbN-type), Group II (HbO-type), and Group III (HbP-type). All bacterial hemoglobins are able to reversibly bind molecular oxygen.

The *Vitreoscilla* hemoglobin (VHb) is the most widely studied bacterial hemoglobin. Recombinant expression of VHb has been reported to improve the growth characteristics and productivity of various proteins in microorganisms grown under microaerobic/oxygen limited conditions (Frey, A. D. and Kallio, P. T., supra; Bollinger et al., *Biotechnol. Prog.* 17:798–808 (2001); and U.S. Pat. No. 5,049,493 to Khosla et al.).

However, a method of using recombinant bacterial hemoglobin expression to alter carotenoid titer and/or production of oxygenated carotenoids (i.e., xanthophylls such as canthaxanthin and/or astaxanthin) has not been reported. Furthermore, a method of using a truncated bacterial hemoglobin, which is structurally unrelated to the *Vitreoscilla* hemoglobin, to improve overall growth and/or carotenoid production in a recombinant microbial host cell has not been reported.

Recombinant expression of truncated bacterial hemoglobins from *Mycobacterium tuberculosis* has been reported (Pathania et al., *J. Biol. Chem.*, 277:15293–15302 (2002)).

Pathania et al. report that the truncated hemoglobins HbN and HbO from *M. tuberculosis* share little structural similarity in their EF-loop regions, suggesting distinct function(s) for each. Recombinant expression of the *M. tuberculosis* HbO resulted in a significant increase in cell mass and higher oxygen update in aerobically growing cells. Given the desirable effects on overall cell growth, there remains a need to identify additional truncated bacterial hemoglobins, especially from non-pathogenic organisms, useful for industrial biotechnology.

The problem to be solved therefore is to provide an isolated nucleic acid molecule encoding a truncated bacterial hemoglobin isolated from a non-pathogenic microorganism capable of increasing the growth rate and/or carotenoid production when recombinantly expressed in a carotenogenic host cell.

SUMMARY OF THE INVENTION

The present invention provides an isolated nucleic acid molecule encoding a truncated bacterial hemoglobin gene capable of increasing the growth rate and/or carotenoid production of a microbial cell when grown under microaerobic conditions. In one embodiment, the present invention comprises an isolated nucleic acid molecule selected from the group consisting of:

(a) an isolated nucleic acid molecule encoding a polypeptide having an amino acid sequence selected from the group consisting of SEQ ID NO:2, 4, and 6;

(b) an isolated nucleic acid molecule that hybridizes with (a) under the following hybridization conditions 0.1X SSC, 0.1% SDS, 65° C. and washed with 2X SSC, 0.1% SDS followed by 0.1X SSC, 0.1% SDS, 65° C.;

(c) an isolated nucleic acid molecule encoding a polypeptide having an amino acid sequence having at least 95% identity to an amino acid sequence selected from the group consisting of SEQ ID NO: 2, 4, and 6; and (d) an isolated nucleic acid molecule that is complementary to (a), (b), or (c).

In another embodiment, the invention also includes a chimeric gene comprising the present isolated nucleic acid molecule operably linked to a suitable regulatory sequence and transformed host cells comprising said chimeric gene.

In another embodiment, a method of increasing the growth rate of a microbial host cell grown under microaerobic conditions is provided comprising:

(a) providing a microbial host cell;

(b) transforming the microbial host cell of (a) with the nucleic acid molecule selected from the group consisting of:

(i) an isolated nucleic acid molecule encoding a polypeptide having an amino acid sequence selected from the group consisting of SEQ ID NOs. 2, 4 and 6;

(ii) an isolated nucleic acid molecule that hybridizes with (a) under the following hybridization conditions: 0.1X SSC, 0.1% SDS, 65° C. and washed with 2X SSC, 0.1% SDS followed by 0.1X SSC, 0.1% SDS, 65° C.;

(iii) an isolated nucleic acid molecule encoding a polypeptide having an amino acid sequence having at least 95% identity to the amino acid sequence selected from the group consisting of SEQ ID NOs: 2, 4 and 6; and (iv) isolated nucleic acid molecule that is complementary to (i), (ii), or (iii); and (c) growing the transformed microbial host cell of (b) under microaerobic conditions whereby the growth rate of the transformed host cell is increased.

In another embodiment, a method is provided to produce carotenoids or increase carotenoid-production (i.e., overall titer and/or conversion rates) in a carotenogenic microbial host cell when grown under microaerobic conditions, said method comprising:

(a) providing a carotenogenic host cell; wherein said carotenogenic host cell comprises more than two copies of a carotenoid ketolase gene or a carotenoid hydroxylase gene;

(b) transforming the carotenogenic host cell of (a) with the nucleic acid molecule selected from the group consisting of:

(i) an isolated nucleic acid molecule encoding a polypeptide having an amino acid sequence selected from the group consisting of SEQ ID NO: 2, 4, and 6;

(ii) an isolated nucleic acid molecule that hybridizes with (a) under the following hybridization conditions: 0.1X SSC, 0.1% SDS, 65° C. and washed with 2X SSC, 0.1% SDS followed by 0.1X SSC, 0.1% SDS, 65° C.;

(iii) an isolated nucleic acid molecule encoding a polypeptide having an amino acid sequence having at least 95% identity to the amino acid sequence selected from the group consisting of SEQ ID NO: 2, 4, and 6; and (iv) isolated nucleic acid molecule that is complementary to (i), (ii), or (iii); and (c) growing the transformed host cell of (b) under microaerobic conditions whereby a carotenoid compound is produced.

A further aspect of the invention provides isolated polypeptides encoded by the present nucleic acid molecules as well as genetic chimera and transformed hosts comprising these polypeptides.

In all aspects of the invention, the transformed host cell is selected from bacteria, yeast, filamentous fungi, and algae. In a further aspect, the bacterial host cell is a methylotrophic bacteria. In yet a further aspect, the methylotrophic bacteria is a high-growth methanotrophic bacteria. In a specific embodiment, the methylotrophic bacteria is selected from *Methylomonas* sp. 16a (ATCC PTA-2402) and derivatives thereof engineered to produce ketocarotenoids and/or hydroxylated carotenoids, such as canthaxanthin and astaxanthin.

BRIEF DESCRIPTION OF THE FIGURES AND SEQUENCE DESCRIPTIONS

FIG. 2 shows the various types of bacterial hemoglobins.

Figure 1:
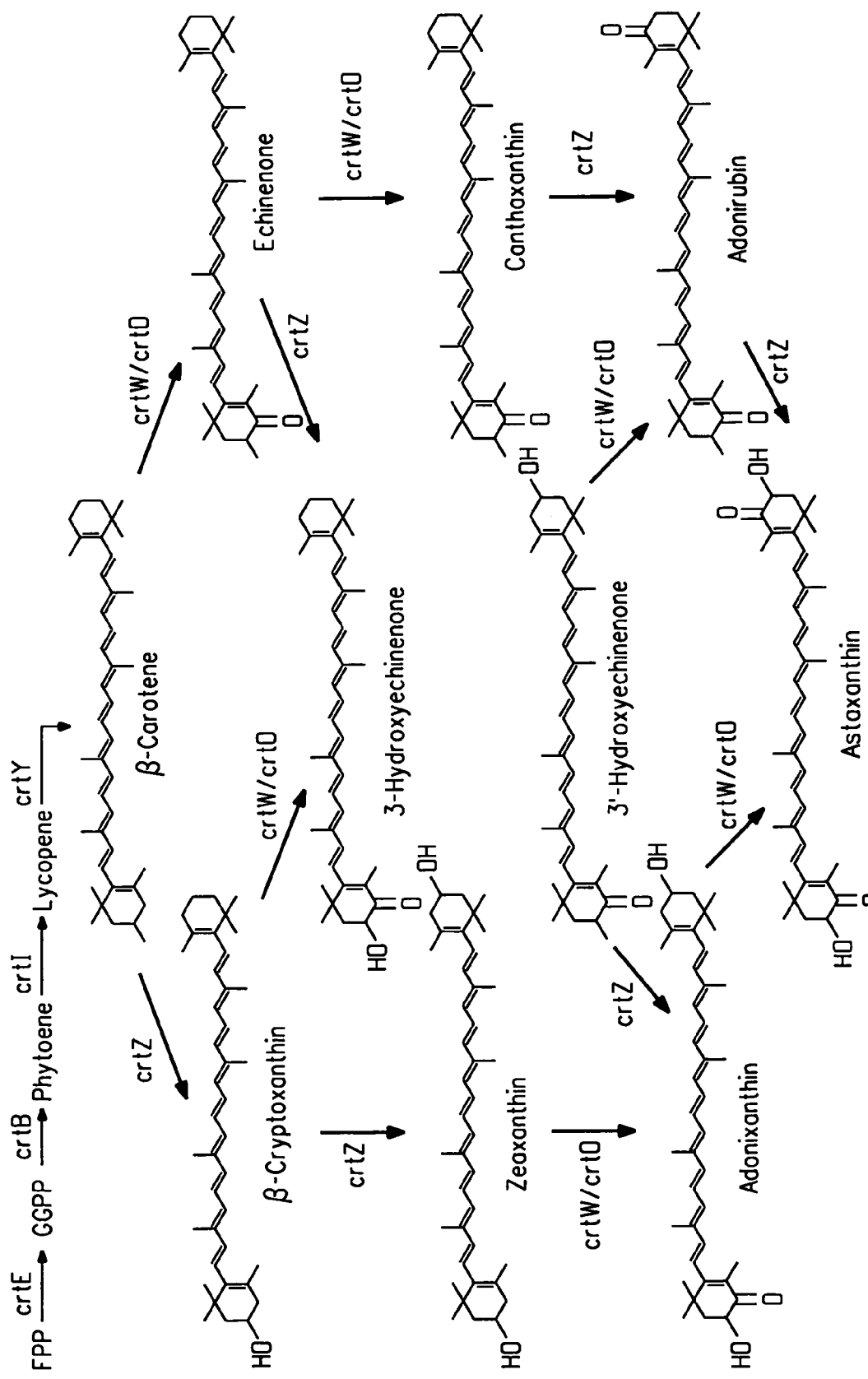
FIG. 1 shows the biosynthetic pathway for the production of canthaxanthin and astaxanthin from a variety of possible precursors via ketolase and/or hydroxylase reactions from β-carotene.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1-Sequence Listing" and "Copy 2 Sequence Listing" The discs contain the following file: CL2879USNA.ST25 having the following size: 31,000 bytes and which was created Jun. 12, 2006.

SEQ ID NO: 1 is the nucleic acid sequence of truncated hemoglobin gene thbN1.

SEQ ID NO: 2 is the deduced amino acid sequence encoded by truncated hemoglobin gene thbN1.

SEQ ID NO: 3 is the nucleic acid sequence of truncated hemoglobin gene thbN2.

SEQ ID NO: 4 is the deduced amino acid sequence encoded by truncated hemoglobin gene thbN2.

SEQ ID NO: 5 is the nucleic acid sequence of truncated hemoglobin gene thbO.

SEQ ID NO: 6 is the deduced amino acid sequence encoded by truncated hemoglobin gene thbO.

SEQ ID NO: 7 is the nucleic acid sequence of promoter Phps isolated from *Methylomonas* sp. 16a (U.S. Ser. No. 10/689,200).

SEQ ID NOs: 8 and 9 are primers used to amplify the Phps1 promoter from *Methylomonas* sp. 16a genomic DNA.

SEQ ID NO: 10 is the nucleic acid sequence of primer gbn1-16a-F.

SEQ ID NO: 11 is the nucleic acid sequence of primer gbn1-16a-R.

SEQ ID NO: 12 is the nucleic acid sequence of primer gbn2-16a-F.

SEQ ID NO: 13 is the nucleic acid sequence of primer gbn2-16a-R.

SEQ ID NO: 14 is the nucleic acid sequence of primer gbo-16a-F.

SEQ ID NO: 15 is the nucleic acid sequence of primer gbo-16a-R.

SEQ ID NO: 16 is the nucleic acid sequence of primer HY-109.

SEQ ID NO: 17 is the nucleic acid sequence of primer HY-107.

SEQ ID NO: 18 is the nucleic acid sequence of plasmid pDCQ343.

SEQ ID NO: 19 is the nucleic acid sequence of primer HY-117.

SEQ ID NO: 20 is the nucleic acid sequence of primer HY-118.

SEQ ID NO: 21 is the nucleic acid sequence for the coding region of the crtW carotenoid ketolase gene isolated from *Sphingomonas melonis* DC18 (U.S. Ser. No. 11/015,433).

SEQ ID NO: 22 is the nucleic acid sequence for the coding region of the crtZ carotenoid hydroxylase gene isolated from *Novosphingobium aromaticivorans* (U.S. Ser. No. 11/200,394).

SEQ ID NO: 23 is the nucleic acid sequence for the coding region of the crtZ carotenoid hydroxylase gene isolated from *Brevundimonas vesicularis* DC263 (U.S. Ser. No. 11/200,394).

SEQ ID NO: 24 is the 16s rRNA gene sequence from *Methylomonas* sp. 16a (ATCC PTA-2402) and derivatives thereof including, but not limited to *Methylomonas* sp. MWM1200 (ATCC PTA-6887), *Methylomonas* sp. orihps333 (ATCC PTA-7122), and *Methylomonas* strain AX1-8.

The following biological deposits were made under the terms of the Budapest Treaty on the International Recognition of the Deposit of Microorganisms for the Purposes of Patent Procedure:

| Depositor Identification Reference | International Depository Designation | Date of Deposit |
| --- | --- | --- |
| *Methylomonas* 16a | ATCC PTA-2402 | Aug. 22, 2000 |
| *Methylomonas* sp. MWM1200 | ATCC PTA-6887 | Jul. 22, 2005 |
| *Methylomonas* sp. orihps333 | ATCC PTA-7122 | Sep. 29, 2005 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC. The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present invention provides a method to increase the carotenoid titer and/or production of oxygenated carotenoids in a carotenogenic host cell by expressing at least one of the present genes encoding an oxygen binding protein (bacterial hemoglobin), especially under microaerobic conditions. The present genes may be overexpressed chromosomally or extrachromosomally to increase carotenoid titer and/or oxygenated carotenoid (ketocarotenoids and/or hydroxylated carotenoids) production under microaerobic conditions.

In one aspect of the present invention, one or more of the present bacterial hemoglobin genes is overexpressed (chromosomally and/or extrachromosomally) to enhance the growth characteristics of recombinant host cells grown under microaerobic conditions. In another aspect, the present bacterial genes are overexpressed on a multicopy plasmid.

In another aspect, the present invention also provides isolated nucleic acid molecules encoding at least one bacterial hemoglobin from *Methylomonas* sp. 16a. In yet another aspect, chimeric gene comprising the present isolated nucleic acid molecules are provided. In a further aspect, host cells recombinantly expressing the present nucleic acid molecules are also provided.

In this disclosure, a number of terms and abbreviations are used. The following definitions are provided:

"Open reading frame" is abbreviated ORF.

"Polymerase chain reaction" is abbreviated PCR.

As used herein, "AST %" means the percentage of astaxanthin produced relative to the total carotenoid content. As shown in the present examples, increased expression of at least of the present bacterial hemoglobin genes in an astaxanthin producing host cell increased the production of astaxanthin.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one aspect, the term "about" means within 20% of the recited numerical value, preferably within 10%, and most preferably within 5%.

The term "invention" or "present invention" as used herein is not mane to be limiting to one aspect of an embodiment of the invention but rather incorporates all aspects and embodiments of the invention as described in the claims and specification.

As used herein, an "isolated nucleic acid molecule" and "isolated nucleic acid fragment" will be used interchangeably and refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the terms "bacterial hemoglobins", "bacterial oxygen binding proteins", and "oxygen binding proteins" are used interchangeably and refer to oxygen-binding proteins belonging to the large superfamily of hemoglobin-like proteins. Bacterial hemoglobins include at least 3 types of hemoglobin-like proteins based on their structure, namely "*Vitreoscilla* hemoglobin" (VHb), the "flavohemoglobins" (FHb), and the "truncated hemoglobins" (trHb) (Frey, A. D., and Kallio, P. T., supra; Bollinger et al., supra). The truncated bacterial hemoglobins are further divided into 3 groups, namely "Group I" (trHbN), "Group II" (trHbO), and "Group III" (trHbP). A search of the *Methylomonas* 16a (ATCC PTA-2402) genome revealed the existence of 3 truncated bacterial hemoglobin genes, two from Group I (i.e., thbN1 and thbN2) and one from Group II (thbO).

As used herein, the terms "microaerobic" and "oxygen-limited" refer to dissolved oxygen concentrations in growth media and/or concentrations occurring within a host cell, which have a detrimental effect on carotenoid production and/or the growth characteristics of the host cell. "Microaerobic" may also refer to any condition where the oxygen concentration in solution is less than 100% oxygen-saturated solution, that is, growth media or intracellular fluid. The oxygen limited conditions may occur extracellularly and/or intracellularly. Moreover, the oxygen limited conditions may occur under conditions where the extracellular dissolved oxygen concentration in the growth medium is saturated while the intracellular oxygen concentration is limited due to quick consumption of large amount of oxygen intracellularly and/or the rate of dissolved oxygen transfer from the extracellular environment into the host cell.

As used herein, the term "pDCQ343" refers to a astaxanthin expression plasmid comprising the carotenoid gene cluster crtWZEYIB (U.S. Ser. No. 11/227,613; herein incorporated by reference). Briefly, the astaxanthin expression plasmid pDCQ343 (SEQ ID NO: 18) was prepared by cloning into pBHR1 (MoBiTec GmbH, Goettingen, Germany) the crtW ketolase from *Sphingomonas melonis* DC18 (U.S. Ser. No. 11/015,433; hereby incorporated by reference; SEQ ID NO: 21) and the crtZ carotenoid hydroxylase (U.S. Ser. No. 11/200,394; SEQ ID NO: 23) from *Brevundimonas vesicularis* DC263 upstream of the crtEYIB gene cluster from *Enterobacteriaceae* DC260 (U.S. Ser. No. 10/808,979; hereby incorporated by reference). The resulting gene cluster, crtWZEYIB was operably linked to the chloramphenicol resistance promoter (Pcat) found on pBHR1.

As used herein, the term "pDCQ363" refers to a plasmid comprising the Phps1 promoter (SEQ ID NO: 7) that results from cloning a nucleic acid fragment comprising the Phps1 promoter into pBHR1 (MoBiTec GmbH).

As used herein, the term "pDCQ385" refers to a plasmid comprising the thbN1 coding sequence operably linked to the Phps1 promoter, disclosed in U.S. Ser. No. 10/689,200 and incorporated herein by reference. The coding sequence of thbN1 was cloned into plasmid pDCQ363 to create pDCQ385.

As used herein, the term "pDCQ385TA" refers to a plasmid expressing the *Methylomonas* sp. 16a thbN1 bacterial hemoglobin gene. The thbN1 gene was cloned into the expression vector pTrcHis2-TOPO® (Invitrogen, Carlsbad, Calif.) to create pDCQ385TA.

As used herein, the term "pDCQ386" refers to a plasmid comprising the thbN2 coding sequence operably linked to the Phps1 promoter. The coding sequence of thbN2 was cloned into plasmid pDCQ363 to create pDCQ386.

As used herein, the term "pDCQ386TA" refers to a plasmid expressing the *Methylomonas* sp. 16a thbN2 bacterial hemoglobin gene. The thbN2 gene was cloned into vector pTrcHis2-TOPO® (Invitrogen) to create pDCQ386TA.

As used herein, the term "pDCQ387" refers to a plasmid comprising the thbO coding sequence operably linked to the Phps1 promoter. The coding sequence of thbO was cloned into plasmid pDCQ363 to create pDCQ387.

As used herein, the term "pDCQ387TA" refers to a plasmid expressing the *Methylomonas* sp. 16a thbO bacterial hemoglobin gene. The thbO gene was cloned into vector pTrcHis2-TOPO® (Invitrogen) to create pDCQ387TA.

As used herein, the term "pDCQ365" refers to a plasmid comprising the crtW from *Sphingomonas melonis* DC18 (SEQ ID NO: 21) and the crtZ from *Novosphingobium aromaticivorans* (SEQ ID NO: 22; U.S. Ser. No. 11/200, 394) expressed under an endogenous *Methylomonas* promoter Phps1 in pDCQ363.

As used herein, the term "pDCQ391" refers to a plasmid comprising the thbO coding sequence operably linked to the Phps1 promoter upstream of the crtWZ genes in pDCQ365. The coding sequence of thbO was cloned into plasmid pDCQ365 to create pDCQ391.

As used herein, the term "pDCQ393" refers to a plasmid comprising the thbN1 coding sequence operably linked to the Phps1 promoter upstream of the crtWZ genes in pDCQ365. The coding sequence of thbN1 was cloned into plasmid pDCQ365 to create pDCQ393.

As used herein, the term "pDCQ394" refers to a plasmid comprising the thbN2 coding sequence operably linked to the Phps1 promoter upstream of the crtWZ genes in pDCQ365. The coding sequence of thbN2 was cloned into plasmid pDCQ365 to create pDCQ394.

As used herein, the term "isoprenoid" or "terpenoid" refers to the compounds derived from the isoprenoid pathway including 10 carbon terpenoids and their derivatives, such as carotenoids and xanthophylls.

As used herein, the term "carotenoid" refers to a compound comprising a polyene backbone which is condensed from a five-carbon isoprene unit. Carotenoids includes both carotenes and oxidation products of carotenes (e.g., xanthophylls).

Carotenoids may be acyclic or terminated with one (monocyclic) or two (bicyclic) cyclic end groups (ionone rings). Carotenoids that are particularly suitable in the present invention are monocyclic and bicyclic carotenoids. The term "carotenoid" may include both carotenes and xanthophylls. A "carotene" refers to a hydrocarbon carotenoid.

As used herein, carotene derivatives that contain one or more oxygen atoms, in the form of hydroxyl or keto groups will be referred to as "oxygenated carotenoids", "oxidized carotenes", or "xanthophylls". These oxidized carotenes will include ketocarotenoids and hydroxylated carotenoids. Examples of these carotenoids include, but are not limited to canthaxanthin, astaxanthin, adonirubin, adonixanthin, echinenone, 3-hydroxyechinenone, 3'-hydroxyechinenone, zeaxanthin, β-cryptoxanthin, and lutein.

As used herein, the term "carotenogenic host cell" is a microbial host cell capable of producing at least one carotenoid. The host cell may naturally produce or be genetically modified to produce the desired carotenoid(s). In one embodiment, the carotenogenic host cell is a host cell capable of producing ketocarotenoids and/or hydroxylated carotenoids. In a further preferred embodiment, the carotenogenic host cell produces canthaxanthin and/or astaxanthin.

As used herein, the term "carotenoid biosynthetic pathway" refers to those genes comprising members of the upper isoprenoid pathway and/or lower carotenoid biosynthetic pathway.

As used herein, The terms "upper isoprenoid pathway", "isoprenoid pathway", and "upper pathway" are used interchangeably and refer to enzymes involved in converting pyruvate and glyceraldehyde-3-phosphate to farnesyl pyrophosphate (FPP). Genes encoding these enzymes include, but are not limited to: the "dxs" gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-D-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol-4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

As used herein, the terms "lower carotenoid biosynthetic pathway" and "lower pathway" will be used interchangeably and refer to those enzymes which convert FPP to a suite of carotenoids. These pathways include those genes and gene products involved in the synthesis of diapophytoene, the first step unique to biosynthesis of $C_{30}$ carotenoids or of phytoene, which represents the first step unique to biosynthesis of $C_{40}$ carotenoids. All subsequent reactions leading to the production of various $C_{30}$–$C_{40}$ carotenoids are included within the lower carotenoid biosynthetic pathway. These genes and gene products comprise all of the "crt" genes including, but not limited to: crtM, crtN1, crtN2, crtE, crtX, crtY, crtI, crtB, crtZ, crtW, crtO, crtA, crtC, crtD, crtF, and crtU. Finally, the term "lower carotenoid biosynthetic enzyme" is an inclusive term referring to any and all of the enzymes in the lower pathway including, but not limited to: CrtM, CrtN1, CrtN2, CrtE, CrtX, CrtY, CrtI, CrtB, CrtZ, CrtW, CrtO, CrtA, CrtC, CrtD, CrtF, and CrtU.

As used herein, "tetraterpenes" or "$C_{40}$ carotenoids" include eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}$ $H_{56}$ structure. Non-limiting examples of $C_{40}$-type carotenoids include: phytoene, lycopene, β-carotene, zeaxanthin, astaxanthin, and canthaxanthin.

As used herein, the term "CrtE" refers to a geranylgeranyl pyrophosphate synthase enzyme encoded by the crtE gene and which converts trans-trans-farnesyl diphosphate and isopentenyl diphosphate to pyrophosphate and geranylgeranyl diphosphate.

As used herein, the term "Idi" refers to an isopentenyl diphosphate isomerase enzyme (E.C. 5.3.3.2) encoded by the idi gene.

As used herein, the term "CrtY" refers to a lycopene cyclase enzyme encoded by the crtY gene, which converts lycopene to β-carotene.

As used herein, the term "CrtI" refers to a phytoene desaturase enzyme encoded by the crI gene. CrtI converts phytoene into lycopene via the intermediaries of phytofluene, ζ-carotene and neurosporene by the introduction of 4 double bonds.

As used herein, the term "CrtB" refers to a phytoene synthase enzyme encoded by the crtB gene which catalyzes the reaction from prephytoene diphosphate to phytoene.

As used herein, the term "CrtZ" refers to a carotenoid hydroxylase enzyme, e.g. β-carotene hydroxylase, encoded by the crtZ gene which catalyzes a hydroxylation reaction. The reaction adds a hydroxyl group to cyclic carotenoids having a β-ionone type ring. This reaction converts cyclic carotenoids, such as β-carotene or canthaxanthin, into the hydroxylated carotenoids zeaxanthin or astaxanthin, respectively. Intermediates in the process typically include β-cryptoxanthin and adonirubin. It is known that CrtZ hydroxylases typically exhibit substrate flexibility, enabling production of a variety of hydroxylated carotenoids depending upon the available substrates (FIG. 1).

As used herein, the term "hydroxyl group" refers to a univalent radical or group comprised of one oxygen and one hydrogen atom ("—OH").

As used herein, the term "hydroxylated carotenoid" refers to carotenoids possessing at least one hydroxyl group on the ionone ring of a cyclic carotenoid. Examples of hydroxylated carotenoids include, but are not limited to zeaxanthin and astaxanthin.

As used herein, the term "CrtW" refers to a β-carotene ketolase enzyme encoded by the crtW gene, which catalyzes an oxidation reaction where a keto group is introduced on the β-ionone type ring of cyclic carotenoids. The term "carotenoid ketolase" or "ketolase" refers to the group of enzymes that can add keto groups to the ionone type ring of cyclic carotenoids. It is known that CrtW ketolases typically exhibit substrate flexibility, enabling production of a variety of -ketocarotenoids depending upon the available substrates (FIG. 1).

As used herein, the term "keto group" or "ketone group" will be used interchangeably and refers to a group in which a carbonyl group is bonded to two carbon atoms: $R_2C=O$ (neither R may be H).

As used herein, the term "ketocarotenoid" refers to carotenoids possessing at least one keto group on the ionone ring of a cyclic carotenoid. Examples of ketocarotenoids include, but are not limited to canthaxanthin and astaxanthin.

As used herein, the term "cyclic carotenoid" refers to a carotenoid having at least one β-ionone ring or β-ionone ring derivative capable of being functionalized by a carotenoid hydroxylase and/or a carotenoid ketolase.

As used herein, "substantially similar" refers to nucleic acid molecules wherein changes in one or more nucleotide bases results in substitution of one or more amino acids, but do not affect the functional properties of the protein encoded by the DNA sequence. "Substantially similar" also refers to nucleic acid molecules wherein changes in one or more nucleotide bases does not affect the ability of the nucleic acid molecule to mediate alteration of gene expression by antisense or co-suppression technology. "Substantially similar" also refers to modifications of the nucleic acid molecules of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by within the present invention. In one embodiment, substantially similar sequences are defined by their ability to hybridize, under stringent conditions (0.1X SSC, 0.1% SDS, 65° C. and washed with 2X SSC, 0.1% SDS followed by 0.1X SSC, 0.1% SDS, 65° C.) with the sequences exemplified herein. In one embodiment, the present invention includes isolated nucleic acid molecules that hybridize under stringent conditions to nucleic acid molecules encoding As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (hereinafter "Maniatis"). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes determine stringency conditions. One set of preferred conditions uses a series of washes starting with 6X SSC, 0.5% SDS at room temperature for 15 min then repeated with 2X SSC, 0.5% SDS at 45° C. for 30 min, and then repeated twice with 0.2X SSC, 0.5% SDS at 50° C. for 30 min. A more preferred set of conditions uses higher temperatures in which the washes are identical to those above except for the temperature of the final two 30 min washes in 0.2X SSC, 0.5% SDS was increased to 60° C. Another preferred set of stringent hybridization conditions is 0.1X SSC, 0.1% SDS, 65° C. and washed with 2X SSC, 0.1% SDS followed by a final wash of 0.1X SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Maniatis, supra, 9.50–9.51). For hybridizations with shorter nucleic acids, i.e., oligonucleotides, the position of mismatches becomes more important, and the length of the oligonucleotide determines its specificity (see Maniatis, supra, 11.7–11.8). In one aspect, the length for a hybridizable nucleic acid is at least about 10 nucleotides. Preferably, a minimum length for a hybridizable nucleic acid is at least about 15 nucleotides; more preferably at least about 20 nucleotides; even more preferably the length is at least 30 nucleotides; and most preferably the length is at least 300 nucleotides in length. Furthermore, the skilled artisan will recognize that the temperature and wash solution salt concentration may be adjusted as necessary according to factors such as length of the probe.

As used herein, the term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing as well as those substantially similar nucleic acid sequences.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.) or the AlignX program of Vector NTI v. 7.0 (Informax, Inc., Bethesda, Md.). Multiple alignment of the sequences can be performed using the Clustal method of alignment (Higgins and Sharp, *CABIOS*, 5:151–153 (1989)) with the default parameters (GAP PENALTY=10, GAP LENGTH PENALTY=10). Default parameters for pairwise alignments using the Clustal method are typically KTUPLE 1, GAP PENALTY=3, WINDOW=5 and DIAGONALS SAVED=5.

In one aspect of the present invention, suitable isolated nucleic acid molecules (isolated polynucleotides of the present invention) encode a polypeptide having an amino acid sequence that is at least about 80% identical to the amino acid sequences reported herein. In another aspect, suitable nucleic acid molecules encode amino acid sequences that are at least about 85% identical to the amino acid sequences reported herein. In yet another aspect, suitable nucleic acid molecules encode amino acid sequences that are at least about 90% identical to the amino acid sequences reported herein. In a further aspect, suitable nucleic acid molecules encode amino acid sequences that are at least 95% identical to the amino acid sequences reported herein. In yet a further aspect, suitable isolated nucleic acid molecules encode amino acid sequences that are at least 99% identical to the amino acid sequences reported herein. Suitable nucleic acid molecules of the present invention not only have the above homologies, but also typically encode a polypeptide having about 115 to about 145 amino acids, preferably about 125 to about 138 amino acids.

As used herein, "codon degeneracy" refers to the nature in the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptides as set forth in SEQ ID NOs: 2, 4, and 6. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, "synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters which cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, "conjugation" refers to a particular type of transformation in which a unidirectional transfer of DNA (e.g., from a bacterial plasmid) occurs from one bacterium cell, the "donor", to another, the "recipient". The process involves direct cell-to-cell contact.

As used herein, the term "carbon substrate" refers to a carbon source capable of being metabolized by host organisms of the present invention and particularly carbon sources selected from the group consisting of monosaccharides, disaccharides, polysaccharides, and one-carbon substrates or mixtures thereof. The term "$C_1$ carbon substrate" refers to any carbon-containing molecule that lacks a carbon-carbon bond. Non-limiting examples are methane, methanol, formaldehyde, formic acid, formate, methylated amines (e.g., mono-, di-, and tri-methyl amine), methylated thiols, and carbon dioxide. In one embodiment, suitable $C_1$ carbon substrates include methane and/or methanol.

As used herein, the term "$C_1$ metabolizer" refers to a microorganism that has the ability to use a single carbon substrate as its sole source of energy and biomass. $C_1$ metabolizers will typically be methylotrophs and/or methanotrophs. The term "$C_1$ metabolizing bacteria" refers to bacteria that have the ability to use a single carbon substrate as their sole source of energy and biomass. $C_1$ metabolizing bacteria, a subset of $C_1$ metabolizers, will typically be methylotrophs and/or methanotrophs. Particularly preferred are those organisms capable of metabolizing methane and/or methanol.

As used herein, the term "methylotroph" means an organism capable of oxidizing organic compounds that do not contain carbon-carbon bonds. Where the methylotroph is able to oxidize $CH_4$, the methylotroph is also a methanotroph. In one embodiment, the bacterial methylotroph is capable of growing on methane and/or methanol (U.S. Pat. No. 6,969,595; herein incorporated by reference).

As used herein, the term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include (but are not limited to) the genera *Methylomonas*, *Methylobacter*, *Methylococcus*, and *Methylosinus*. In one embodiment, the methanotroph is capable of growing on methane and/or methanol.

As used herein, the term "high growth methanotrophic bacterial strain" refers to a bacterium capable of growth with methane or methanol as the sole carbon and energy source and which possesses a functional Embden-Meyerhof carbon flux pathway, resulting in a high rate of growth and yield of cell mass per gram of $C_1$ substrate metabolized (U.S. Pat. No. 6,689,601; herein incorporated by reference). In another embodiment, the high growth methanotrophic bacterium is *Methylomonas* sp. 16a (ATCC PTA-2402) and derivatives thereof. In one aspect, the terms "mutant derivatives", "derivatives of *Methylomonas* sp. 16a", and "derivatives thereof" will be used to refer to *Methylomonas* strains developed from *Methylomonas* sp. 16a (ATCC PTA-2402). In a further aspect, the derivatives of *Methylomonas* sp. 16a are comprised of the 16s rRNA gene sequence as represented by SEQ ID NO: 24 (U.S. Pat. No. 6,689,601). In yet another embodiment, the high growth methanotrophic bacterial strain utilizes methanol and/or methane as a primary carbon source.

As used herein, the term "MWM1200 (Δcrt cluster promoter+ΔcrtN3)" refers to a mutant of *Methylomonas* sp. 16a in which the crt cluster promoter and the crtN3 gene have been disrupted. Disruption of the native $C_{30}$ carotenoid-biosynthetic pathway results in suitable background for engineering $C_{40}$ carotenoid production. The *Methylomonas* MWM1200 strain was previously created and is a suitable carotenoid production host (U.S. Ser. No. 10/997,844, incorporated herein by reference; ATCC PTA-6887). The term "pigmentless" or "white mutant" refers to a *Methylomonas* sp. 16a bacterium wherein the native pink pigment, e.g., a $C_{30}$ carotenoid, is not produced. Thus, the bacterial cells appear white in color, as opposed to pink.

As used herein, the term "astaxanthin-producing *Methylomonas* strain" refers to an astaxanthin-producing derivative strain of *Methylomonas* MWM1200 (U.S. Ser. No. 10/997,844). Astaxanthin-producing *Methylomonas* strains can be prepared by chromosomally-integrating astaxanthin biosynthesis genes, at least one copy of each of the following carotenoid biosynthesis crtE, crtY, crtI, crtB, crtW, and crtZ, in a pigmentless *Methylomonas* sp. 16a background.

As used herein, the term "*Methylomonas* sp. orihps333" refers to a canthaxanthin producing derivative of *Methylomonas* MWM1200 ATCC PTA-6887 created by integrating a canthaxanthin gene cluster, operably linked to the hps promoter isolated from *Methylomonas* sp. 16a (U.S. Ser. No. 10/689,200), into the ori region of the *Methylomonas* chromosome (See pending U.S. provisional application entitled "ANIMAL FEED PIGMENTS FROM METHANOTROPHIC MICROBIAL BIOMASS" filed Mar. 9, 2006; herein incorporated by reference). *Methylomonas* sp. orihps333 was deposited to the American Type Culture Collection under accession number PTA-7122.

As used herein, the term *Methylomonas* strain AX1-8 refers to an astaxanthin-producing strain derived from *Methylomonas* sp. 16a comprising 1) a chromosomally integrated crtWZ gene cluster (crtW from *Sphingomonas melonis* DC18 (SEQ ID: 21) and crtZ from *Brevundimonas vesicularis* DC263 (SEQ ID NO: 23), operably linked to the hps promoter (SEQ ID NO: 7), into the aid region (U.S. Ser. No. 10/997,844 herein incorporated by reference) of *Methylomonas* sp. orihps333 (ATCC PTA-7122), and 2) an additional crtZ gene (crtZ from *Brevundimonas vesicularis* DC263) (operably linked to an hps promoter) chromosomally integrated in the tig region (U.S. Ser. No. 11/070,080; herein incorporated by reference) of the *Methylomonas* chromosome.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

Discovery of Genes Coding for Bacterial Oxygen Binding Proteins

The present invention provides bacterial oxygen binding proteins (truncated-type bacterial hemoglobins) and isolated from *Methylomonas* sp. 16a (ATCC PTA-2402). Recombinant and/or increased expression of the three truncated hemoglobin genes have been shown to increase the overall growth characteristics of a host cell grown under-microaerobic conditions. It has also been shown that increased expression of the present bacterial hemoglobin genes increases the production of oxygenated carotenoids when expressed with a crtWZ gene cluster under microaerobic conditions. The present sequence may be used in vitro and in vivo in recombinant hosts for the production of oxygenated compounds, i.e., xanthophylls, from cyclic carotenoid compounds.

Comparison of the *Methylomonas* sp. 16a thbN1 nucleotide base and deduced amino acid sequence (SEQ ID NOs: 1 and 2) to public databases reveals that the most similar, known sequence has about 81% identity to the amino acid sequence reported herein using the BLASTXnr search (Table 4).

Comparison of the *Methylomonas* sp. 16a thbN2 nucleotide base and deduced amino acid sequence (SEQ ID NOs: 3 and 4) to public databases reveals that the most similar known sequence has about 64% identity to the amino acid sequence reported herein using the BLASTXnr search (Table 4).

Comparison of the *Methylomonas* sp. 16a thbO nucleotide base and deduced amino acid sequences (SEQ ID NOs: 5 and 6) to public databases reveals that the most similar known sequence has about 62% identity to the amino acid sequence reported herein using the BLASTXnr search (Table 4).

Accordingly, preferred amino acid fragments are at least about 85% identical to the amino acid sequences herein, more preferred amino acid sequences are at least about 90% identical to the amino acid fragments reported herein, even more preferred amino acid sequences are at least about 95% identical to the amino acid fragments reported herein, and most preferred are nucleic acid molecules that are at least 99% identical to the amino acid molecules reported herein.

Isolation of Homologs

The nucleic acid molecules of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci.* USA 82:1074 (1985)) or strand displacement amplification (SDA, Walker, et al., *Proc. Natl. Acad. Sci.* U.S.A., 89:392 (1992)).

For example, genes encoding proteins or polypeptides similar to those of the instant invention may be isolated directly by using all or a portion of the instant nucleic acid molecules as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra). Moreover, the entire sequences may be used directly to synthesize DNA probes by methods known to the skilled artisan such as random primers DNA labeling, nick translation, end-labeling techniques, or RNA probes using available in vitro transcription systems. In addition, specific primers can be designed and used to amplify a part of or the full-length of the instant sequences. The resulting amplification products can be labeled directly during or after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. See Thein and Wallace, "The use of oligonucleotides as specific hybridization probes in the Diagnosis of Genetic Disorders", in *Human Genetic Diseases: A Practical Approach*, K. E. Davis Ed., (1986) pp. 33–50 IRL Press, Herndon, Va.; Rychlik, W. (1993) In White, B. A. (ed.), *Methods in Molecular Biology*, Vol.15, pages 31–39, "PCR Protocols: Current Methods and Applications", Humania Press, Inc., Totowa, N.J.

Generally two short segments of the instant sequences may be used as primers in a polymerase chain reaction to amplify longer nucleic acid molecules encoding homologous genes from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor of a eukaryotic gene. In the case of microbial genes which lack polyadenylated mRNA, random primers may be used. Random primers may also be useful for amplification from DNA.

Alternatively, the second primer sequence may be based upon sequences derived from the cloning vector. For example, the skilled artisan can follow the RACE protocol (Frohman et al., *Proc. Natl. Acad. Sci.* U.S.A, 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci.* U.S.A, 86:5673 (1989); Loh et al., *Science* 243:217 (1989)).

The present sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be exact. Hybridization with mismatches does occur between not exactly complementary molecules, which results in a fraction of the bases in the hybridized region being paired with a non-complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A., *Adv. Immunol,.* 36:1 (1984); Maniatis, supra).

Bacterial Hemoglobins

Bacterial hemoglobins are a subset of the larger hemoglobin-like superfamily. They have been reported to be involved in intracellular storage and delivery of oxygen (Frey, A. D., and Kallio, P. T., supra). The genes encoding bacterial hemoglobins are typically expressed in response to oxygen limitation or oxidative and nitrosative stress.

Three different types of bacterial hemoglobins have been reported: the *Vitreoscilla* hemoglobin (VHb), flavohemoglobins (FHb), and truncated hemoglobins (trHb) (FIG. 2). All three types of bacterial hemoglobins have a high affinity for molecular oxygen and are capable of reversibly binding $O_2$. The bacterial hemoglobins act as sequesters for $O_2$, thereby increasing intracellular $O_2$ tension.

The *Vitreoscilla* hemoglobin and flavohemoglobins share sequence homology and structural similarity in their globin domain. The *Vitreoscilla* Hb is encoded by the vhb gene, encoding a protein of about 15.7 kDa. VHb is a homodimeric hemoglobin. The role of VHb is generally believed to be associated with oxygen binding and transport. The *Vitreoscilla* Hb is the most well-studied bacterial hemoglobin. When expressed in recombinant host cells grown under oxygen-limited conditions, it has been reported to increase overall cell growth and improve productivity (Frey, A. D. and Kallio, P. T., supra)

Flavohemoglobins share sequence homology and structural similarity to the globin domain of the *Vitreoscilla* hemoglobin. FHbs are typically have a molecular mass of about 44 kDA and comprise an additional reductase domain. Flavohemoglobins are believed to be also involved in the detoxification of nitric oxide, that is in aerobic detoxification.

The truncated bacterial hemoglobins ("trHb") are a family of small-oxygen binding heme proteins that are found in eubacteria, protozoa, cyanobacteria, and plants and are divided into 3 groups (Group I, "trHbN"; Group II, "trHbO"; and Group III, "trHbP"). The truncated hemoglobins are significantly shorted and share very little sequence homology with *Vitreoscilla*-like hemoglobins and flavohemoglobins. As such, they comprise a distinct family of hemoglobins within the hemoglobin superfamily (Wittenberg et al., *J. Biol. Chem.*, 277(2):871–874 (2002)).

All truncated hemoglobins have a unique 2-on-2 version of the globin fold when compared to the classical 3-on-3 α-helix sandwich found in non-truncated hemoglobins (Wittenberg et al., supra). The exact role of truncated hemoglobins is not conclusively known. However they may be involved in oxygen transport and storage. However, a structural and biochemical comparison of the HbO and HbN truncated bacterial hemoglobins from *Mycobacterium tuberculosis* suggests different functions for these hemoglobins (Pathania et al., supra). Recombinant expression of a bacterial hemoglobin to increase carotenoid production in host cell under oxygen-limited conditions has not been reported.

A search of the *Methylomonas* 16a (ATCC PTA-2402) genome identified 3 truncated bacterial hemoglobin genes, 2 from Group I (thbN1 and thbN2) and one from Group II (thbO) (FIG. 2; Table 4). The amino acid sequence of THbN1 shares 69% identity with the amino acid sequence of THbN2. ThbO shares only 17–20% amino acid identity with THbN1 and THbN2.

Recombinant Expression—Microbial

The genes and gene products of the instant sequences may be produced in heterologous host cells, particularly in the cells of microbial hosts. Expression in recombinant microbial cells under oxygen-limited conditions may be useful for: the expression of various pathway intermediates; the modulation of pathways already existing in the host, or the synthesis of new products heretofore not possible using the host. In one aspect, recombinant expression of a bacterial hemoglobin gene is useful to increase carotenoid production, especially oxygenated carotenoid production, in a host cell under oxygen-limited conditions.

Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. Transcription, translation and the protein biosynthetic apparatus remain invariant relative to the cellular feedstock used to generate cellular biomass; functional genes will be expressed regardless. Examples of host strains include, but are not limited to bacterial, fungal or yeast species such as *Aspergillus, Trichoderma, Saccharomyces, Pichia, Phaffia, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. In one embodiment, bacterial host strains include *Escherichia, Bacillus,* and *Methylomonas*. In a further embodiment, the bacterial host strain is a methylotrophic bacteria. In yet a further embodiment, the bacterial host strain is a high-growth methanotrophic bacteria. In still yet a further embodiment, the high-growth methanotrophic bacteria is *Methylomonas* sp. 16a and derivatives thereof.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. Preferably, the present genes are expressed under oxygen-limited (microaerobic) conditions. In addition, the regulation of growth rate may be affected by the addition, or not, of specific regulatory molecules to the culture and which are not typically considered nutrient or energy sources.

In a different aspect, the introduction of a chimeric gene under the control of an appropriate promoter and encoding a bacterial oxygen binding protein will increase carotenoid production and/or the growth characteristic of the microbial host cell when grown under the microaerobic growth conditions specified herein. In another aspect, the expressed bacterial oxygen binding proteins are those classified as a a truncated bacterial hemoglobin (trHb). In yet another aspect, the oxygen binding protein is classified as a Group I (HbN-type) or Group II (HbO-type) truncated hemoglobin. It is contemplated that it will be useful to express this gene both in natural host cells as well as heterologous hosts. Increased expression of the gene encoding the bacterial oxygen binding protein represented by SEQ ID NOs: 2, 4, and 6 into native host will result in altered carotenoid production under microaerobic growth conditions. As used herein, altered carotenoid production means a change in overall carotenoid titer and/or production of oxygenated carotenoids. In a further aspect, expression of a truncated bacterial hemoglobin gene encoding a polypeptide having an amino acid sequence having at least 95% identity to an amino acid sequence selected from the group consisting of SEQ ID NOs: 2, 4 and 6 increase oxygenated carotenoid production in a host cell under oxygen-limited conditions. In another aspect, the increase in oxygenated carotenoid production is measured by the relative increase in conversion of one or more of the various intermediates shown in FIG. 1 to the desired product (e.g. canthaxanthin and/or astaxanthin) under microaerobic conditions. In still a further aspect, the increase in carotenoid production occurs in a transformed carotenogenic host cell grown under microaerobic conditions, wherein said cell comprises more than two copies of a crtW carotenoid ketolase and/or crtZ hydroxylase gene. In a further aspect, the percent increase in carotenoid production/conversion and/or growth rate is at least 5%, preferably at least 10%, more preferably at least 25% relative to an unmodified host cell grown under similar microaerobic conditions.

Specific carotenoids that will be produced by the present invention include, but are not limited to, zeaxanthin, astaxanthin, canthaxanthin, echinenone, β-cryptoxanthin, 3-hydroxyechinenone, 3'-hydroxyechinenone, adonirubin, adonixanthin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal, lutein, and other xanthophylls. Of particular interest is the production of astaxanthin and canthaxanthin, the synthesis of which is shown in FIG. 1.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from-genes homologous to the transformed host cell and/or native to the production host, although such control regions need not be so derived.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*, and promoters isolated from the nrtA, glnB, moxF, glyoxlI, htpG, and hps genes useful for expression in *Methylomonas* (U.S. Ser. No. 10/689,200, incorporated herein by reference). Additionally, promoters such as the chloramphenicol resistance gene promoter may also be useful for expression in *Methylomonas*.

Termination control regions may also be derived from various genes native to the preferred hosts. A termination site may be unnecessary, but is most preferred.

Knowledge of the sequence of the present gene will be useful in manipulating the overall growth characteristics and/or carotenoid production in any microorganism organism having such a pathway when grown under microaerobic conditions. Methods of manipulating genetic pathways are common and well known in the art. Selected genes in a particular pathway may be upregulated or down-regulated by a variety of methods. Additionally, competing pathways may be eliminated or sublimated by gene disruption and similar techniques.

Once a key genetic pathway has been identified and sequenced, specific genes may be upregulated to increase the output of the pathway. For example, additional copies of the targeted genes may be introduced into the host cell on multicopy plasmids such as pBR322. Optionally, multiple genes encoding bacterial oxygen binding proteins may be chromosomally expressed to increase the transformed host cell's growth characteristics and/or carotenoid production. However, stable chromosomal expression of multiple genes generally requires that the coding sequences of the genes used comprise nucleotide sequences having low to moderate sequence identity to one another. The present genes encoding bacterial oxygen binding proteins exhibit relative low to moderate nucleotide sequence identity to all previously reported bacterial hemoglobin genes, especially the structurally-unrelated *Vitreoscilla* hemoglobin.

When it is desired to regulate expression of the target gene, say when a pathway operates at a particular point in a cell cycle or during a fermentation run, regulated or inducible promoters may used to replace the native promoter of the target gene. Or in some cases the native or endogenous promoter may be modified to increase gene expression. For example, endogenous promoters can be altered in vivo by mutation, deletion, and/or substitution (see U.S. Pat. No. 5,565,350 to Kmiec; Zarling et al., PCT/US93/03868).

Methylotrophs and *Methylomonas* sp. 16a as Microbial Hosts

There are a number of microorganisms that utilize single carbon substrates as their sole energy source. Such microorganisms are referred to herein as "$C_1$ metabolizers". These organisms are characterized by the ability to use carbon substrates lacking carbon to carbon bonds as a sole source of energy and biomass. These carbon substrates include, but are not limited to, methane, methanol, formate, formaldehyde, formic acid, methylated amines (e.g., mono-, di- and tri-methyl amine), methylated thiols, carbon dioxide, and other reduced carbon compounds lacking any carbon-carbon bonds. Preferred substrates include methane and/or methanol (U.S. Pat. No. 6,969,595).

All $C_1$ metabolizing microorganisms are generally classified as methylotrophs. Methylotrophs may be defined as any organism capable of oxidizing organic compounds that do not contain carbon-carbon bonds. Three kinds of methyltrophs are:

Facultative methylotrophs, which have the ability to oxidize organic compounds which do not contain carbon-carbon bonds, but may also use other carbon substrates such as sugars and complex carbohydrates for energy and biomass. Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds*, [Int. Symp.], 7th (1993), pp 285–302. Murrell, J. Collin and Don P. Kelly, Eds. Intercept: Andover, UK; Madigan et al., *Brock Biology of Microorganisms*, 8th ed., Prentice Hall: UpperSaddle River, N.J. (1997)).

Obligate methylotrophs, which can use only organic compounds that do not contain carbon-carbon bonds for the generation of energy.

Obligate methanotrophs, which are those obligate methylotrophs that have the distinct ability to oxidize methane.

Additionally, the ability to use single carbon substrates is not limited to bacteria but extends also to yeasts and fungi.

A number of yeast genera are able to use single carbon substrates as energy sources in addition to more complex materials, i.e., the methylotrophic yeasts.

Although a large number of these methylotrophic organisms are known, few of these microbes have been successfully harnessed in industrial processes for the synthesis of materials. And, although single carbon substrates are cost-effective energy sources, difficulty in genetic manipulation of these microorganisms as well as a dearth of information about their genetic machinery has limited their use primarily to the synthesis of native products.

Despite these difficulties, many methanotrophs contain an inherent isoprenoid pathway that enables them to synthesize pigments and which may be engineered for the production of non-endogenous isoprenoid compounds. Since methanotrophs can use the single carbon substrates of methane and/or methanol as an energy source, it is possible to produce carotenoids at low cost in these organisms. One such example wherein a methanotroph is engineered for production of one or more carotenoids is described in U.S. Pat. No. 6,969,595; incorporated herein by reference.

In one embodiment, the present invention provides methods for the expression of genes encoding bacterial oxygen binding proteins in microorganisms that are able to use single carbon substrates as a sole energy source. The host microorganism may be any $C_1$ metabolizer that has the ability to synthesize farnesyl pyrophosphate (FPP) as a metabolic precursor for carotenoids. More specifically, facultative methylotrophic bacteria suitable in the present invention include, but are not limited to, *Methylophilus, Methylobacillus, Methylobacterium, Hyphomicrobium, Xanthobacter, Bacillus, Paracoccus, Nocardia, Arthrobacter, Rhodopseudomonas*, and *Pseudomonas*. Specific methylotrophic yeasts useful in the present invention include, but are not limited to: *Candida, Hansenula, Pichia, Torulopsis*, and *Rhodotorula*. Exemplary methanotrophs include, but are not limited to the genera *Methylomonas, Methylobacter, Methylococcus, Methylosinus, Methylocyctis, Methylomicrobium*, and *Methanomonas*.

Of particular interest in the present invention are high growth obligate methanotrophs having an energetically favorable carbon flux pathway. For example, a specific strain of methanotroph having several pathway features that make it particularly useful for carbon flux manipulation is known as *Methylomonas* 16a (ATCC PTA 2402) (U.S. Pat. No. 6,689,601). This strain, derivatives of *Methylomonas* sp. 16a, and other related methylotrophs are preferred microbial hosts for expression of the gene products of this invention. That is, they are useful for the production of $C_{40}$ carotenoids, especially the production of ketocarotenoid and/or hydroxylated carotenoids such as canthaxanthin and astaxanthin.

Transformation of C1 Metabolizing Bacteria

Electroporation has been used successfully for the transformation of: *Methylobacterium extorquens* AM1 (Toyama, H., et al., *FEMS Microbiol. Lett.* 166:1–7 (1998)), *Methylophilus methylotrophus* AS1 (Kim, C. S., and T. K. Wood., *Appl. Microbiol. Biotechnol.* 48:105–108 (1997)), and *Methylobacillus* sp. strain 12S (Yoshida, T. et al., *Biotechnol. Lett.*, 23: 787–791 (2001)). Transformation of *Methylomonas* sp. 16a (ATCC PTA-2402) and derivatives thereof using bacterial conjugation has been reported (see U.S. Ser. Nos. 10/997,844 and 10/997,308; each herein incorporated by reference).

Bacterial conjugation is frequently more readily amenable for the transfer of genes into C1 metabolizing bacteria. This bacterial conjugation process involves simply mixing together "donor" and "recipient" cells in close contact with one another. Conjugation occurs by formation of cytoplasmic connections between donor and recipient bacteria, with direct transfer of newly synthesized donor DNA into the recipient cells. As is well known in the art, the recipient in a conjugation is defined as any cell that can accept DNA through horizontal transfer from a donor bacterium. The donor in conjugative transfer is a bacterium that contains a conjugative plasmid, conjugative transposon, or mobilizable plasmid. The physical transfer of the donor plasmid can occur in one of two fashions, as described below:

First, in cases when only a donor and recipient are required for conjugation, the plasmid to be transferred is a self-transmissible plasmid that is both conjugative and mobilizable. Thus, it carries both tra genes and genes encoding the Mob proteins. The process includes the following: Double-strand plasmid DNA is nicked at a specific site in oriT. A single-strand DNA is released to the recipient through a pore or pilus structure. A DNA relaxase enzyme cleaves the double-strand DNA at oriT and binds to a released 5' end, forming a relaxosome as the intermediate structure. Subsequently, a complex of auxiliary proteins assemble at oriT to facilitate the process of DNA transfer.

Alternatively, in a "triparental" conjugation donor cells, recipient cells, and a "helper" plasmid participate. The donor cells carry a mobilizable plasmid or conjugative transposon. Mobilizable vectors contain an oriT, a gene encoding a nickase, and have genes encoding the Mob proteins. The Mob proteins alone are insufficient to achieve the transfer of the genome. Thus, mobilizable plasmids are not able to promote their own transfer unless an appropriate conjugation system is provided by a helper plasmid, located within either the donor or a "helper" cell). The conjugative plasmid is needed for the formation of the mating pair and DNA transfer, since the plasmid encodes proteins for transfer (Tra) that are involved in the formation of the pore or pilus.

Examples of successful conjugations involving C1 metabolizing bacteria are disclosed in Stolyar et al. (*Mikrobiologiya* 64(5): 686–691 (1995)); Motoyama, H. et al. (*Appl. Micro. Biotech.* 42(1): 67–72 (1994)); Lloyd, J. S. et al. (*Archives of Microbiology* 171(6): 364–370 (1999)); and Odom, J. M. et al. (U.S. Pat. No. 6,969,595).

Industrial Production

A variety of culture methodologies may be applied. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process, the media is inoculated with the desired organism or organisms and growth or metabolic activity may occur without adding anything further to the system. Typically, however, a "batch" culture is batch with respect to the addition of carbon source and attempts are often made to control factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system except that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

Commercial production of the desired products may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.*, 153:485–489 (1990)). Hence, it is contemplated that the source of carbon utilized in the present invention may encompass a wide variety of carbon containing substrates and will only be limited by the choice of organism.

Genes Involved in Carotenoid Production.

The present invention provides a method to increase carotenoid production, particularly oxygenated carotenoids, by expression of a truncated bacterial hemoglobin in a host cell, especially when grown under oxygen-limited (microaerobic) conditions. The enzymatic pathway involved in the biosynthesis of carotenoids is known in the art and can be viewed in two parts: the upper isoprenoid pathway providing for the conversion of pyruvate and glyceraldehyde-3-phosphate to farnesyl pyrophosphate (FPP) and the lower carotenoid biosynthetic pathway, which provides for the synthesis of phytoene and all subsequently produced carotenoids.

The key division between the two pathways concerns the synthesis of farnesyl pyrophosphate. When the upper pathway naturally results in FPP—as it does in many microorganisms—it will only be necessary to introduce genes that govern the lower pathway to synthesize the desired carotenoid and/or to ensure that cellular FPP levels suffice for the production of carotenoids by lower pathway genes. When the upper pathway is not present in the host cell, it will be necessary to introduce the genes necessary for the production of FPP. The upper and lower pathway is discussed separately.

The Upper Isoprenoid Pathway

Isoprenoid biosynthesis occurs through one of two pathways and results in the common $C_5$ isoprene sub-unit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.*, 111:135–140 (1993); Rohmer et al., *Biochem.*, 295:517–524 (1993); Schwender et al., *Biochem.*, 316:73–80 (1996); and Eisenreich et al., *Proc. Natl. Acad. Sci.* USA, 93:6431–6436 (1996)).

Many steps in the mevalonate-independent isoprenoid pathway are known. See, e.g., Cole et al. (*Nature*, 393: 537–544 (1998), reporting the initial steps of the alternate pathway leading to the production of IPP in *Mycobacterium tuberculosis*. The first step of this pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr (ispC). 2-C-methyl-D-erythritol-4-phosphate is subsequently converted into 4-diphosphocytidyl-2C-methyl-D-erythritol in a CTP-dependent reaction by the enzyme encoded by the nonannotated gene ygbP. Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This results in 4-diphosphocytidyl-2C-methyl-D-erythritol 2-phosphate. The ychB gene was renamed as ispE, also as a part of the isp gene cluster (SwissProtein Accession #P24209). YgbB converts 4-diphosphocytidyl-2C-methyl-D-erythritol 2-phosphate to 2C-methyl-D-erythritol 2,4-cyclodiphosphate in a CTP-dependent manner. This gene has also been recently renamed to ispF (SwissProtein Accession #P36663) and belongs to the isp gene cluster.

The enzymes encoded by the gcpE (ispG) and lytB (ispH) genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene. However, this enzyme is not essential for survival and may be absent in some bacteria using 2-C-methyl-D-erythritol 4-phosphate (MEP) pathway. Recent evidence suggests that the MEP pathway branches before IPP and separately produces IPP and DMAPP via the lytB gene product. A lytB knockout mutation is lethal in *E. coli* except in media supplemented with both IPP and DMAPP.

The synthesis of FPP occurs via the isomerization of IPP to dimethylallyl pyrophosphate. This reaction is followed by a sequence of two prenyltransferase reactions catalyzed by ispA, leading to the creation of geranyl pyrophosphate (GPP), a 10-carbon molecule and farnesyl pyrophosphate (FPP), a 15-carbon molecule.

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the first step in the lower carotenoid biosynthetic pathway is considered to begin with the prenyltransferase reaction converting farnesyl pyrophosphate (FPP) to geranylgeranyl pyrophosphate (GGPP). The gene crtE, encoding GGPP synthetase, is responsible for this prenyltransferase reaction which adds IPP to FPP to produce the 20-carbon molecule GGPP. A condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

Lycopene, which imparts "red" colored spectra, is produced from phytoene through four sequential dehydrogenation reactions by the removal of eight atoms of hydrogen, catalyzed by the gene crtI encoding phytoene desaturase. Intermediaries in this reaction are phytofluene, zeta-carotene, and neurosporene.

Lycopene cyclase (crtY) converts lycopene to β-carotene. However, additional genes may be used to create a variety of other carotenoids. For example, β-carotene is converted to zeaxanthin via a hydroxylation reaction resulting from the activity of β-carotene hydroxylase (encoded by the crtZ gene). β-cryptoxanthin is an intermediate in this reaction (FIG. 1).

β-carotene can be converted to canthaxanthin by β-carotene ketolase encoded by either the crtW or crtO genes. Echinenone is typically an intermediate in this reaction. Canthaxanthin can be converted to astaxanthin by β-carotene hydroxylase encoded by the crtZ gene. Adonbirubrin is an intermediate in this reaction (FIG. 1).

Preferred sources of the carotenoid genes are from *Pantoea agglomerans* DC404 (U.S. Ser. No. 10/808,807), *Enterobacteriaceae* DC260 (U.S. Ser. No. 10/808,979), *Brevundimonas vesicularis* DC263 (U.S. Ser. No. 11/015, 433), and *Sphingomonas melonis* DC18 (U.S. Ser. No. 11/015,433).

By using various combinations of the above mentioned carotenoid biosynthesis genes, numerous different carotenoids and carotenoid derivatives could be made using the methods described herein, provided that sufficient sources of FPP are available in the host organism. For example, the gene cluster crtEYIB enables the production of β-carotene. Addition of the crtZ to crtEYIB enables the production of zeaxanthin. Further addition of crtW to crtEYIBZ enables the production of astaxanthin.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples illustrate, and do not exclusively define, the invention. From the above discussion and these Examples, one skilled in the art can ascertain the essential characteristics of this invention and can make changes and modifications of the invention to adapt it to various usages and conditions.

General Methods

Standard recombinant DNA and molecular cloning techniques used in the Examples are well known in the art and are described by Maniatis, (supra) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Brock (supra). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), Invitrogen (Carlsbad, Calif.) or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used, the gap creation default value of 12, and the gap extension default value of 4 were used. Where the GCG "Gap" or "Bestfit" programs were used, the default gap creation penalty of 50 and the default gap extension penalty of 3 were used. In any case where GCG program, parameters were not prompted for, in these or any other GCG program, default values were used.

The meaning of abbreviations is as follows: "sec" means second(s), "min" means minute(s), "h" means hour(s), "d" means day(s), "µL" means microliter, "mL" means milliliters, "L" means liters, "µM" means micromolar, "mM" means millimolar, "M" means molar, "mmol" means millimole(s), "µmole" mean micromole", "g" means gram, "µg" means microgram, "ng" means nanogram, "U" means units, "bp" means base pairs, "kB" means kilobase, "psi" means pounds per square inch, "EDTA" means ethylenediaminetetraacetic acid.

Plasmids

For ease of understanding, the following plasmids were used in these studies and reported in Table 1.

TABLE 1

Plasmids used in this application

| Plasmid | Backbone | Expressed genes and Organism* |
|---|---|---|
| pTrcHis2-TOPO® TA | vector | None |
| pDCQ385TA | pTrcHis2-TOPO | thbN1(*Methylomonas*) |
| pDCQ386TA | pTrcHis2-TOPO | thbN2(*Methylomonas*) |
| pDCQ387TA | pTrcHis2-TOPO | thbO(*Methylomonas*) |
| pBHR1 | vector | None |
| pDCQ385 | pBHR1 | thbN1(*Methylomonas*) |
| pDCQ386 | pBHR1 | thbN2(*Methylomonas*) |
| pDCQ387 | pBHR1 | thbO(*Methylomonas*) |
| pDCQ365 | pBHR1 | crtW(DC18)crtZ(*Sphingomonas*) |
| pDCQ391 | pBHR1 | thbO(*Methylomonas*) crtW(DC18)crtZ(*Sphingomonas*) |
| pDCQ393 | pBHR1 | thbN1(*Methylomonas*) crtW(DC18)crtZ(*Sphingomonas*) |
| pDCQ394 | pBHR1 | thbN2(*Methylomonas*) crtW(DC18)crtZ(*Sphingomonas*) |

*Organism refers to that from which the gene was isolated.

Microbial Cultivation and Associated Analyses for *Methylomonas* 16a

The following summarizes the standard conditions used for growth of *Methylomonas* sp. 16a (ATCC# PTA-2402) and derivatives thereof, as described in U.S. Pat. No. 6,689,601, incorporated herein by reference. Briefly, the following conditions were used throughout the experimental Examples for treatment of *Methylomonas* sp., unless conditions were specifically mentioned to be different.

*Methylomonas* sp. is typically grown in serum stoppered Wheaton bottles (Wheaton Scientific, Wheaton Ill.) using a gas/liquid ratio of at least 8:1 (i.e., 20 mL of Nitrate liquid "BTZ-3" media of 160 mL total volume). The standard gas phase for cultivation contained 25% methane in air. These conditions comprise growth conditions and the cells are referred to as growing cells. In all cases, the cultures were grown at 30° C. with constant shaking in a Lab-Line rotary shaker unless otherwise specified.

For assays of carotenoid composition, *Methylomonas* transconjugants were cultured in a 24-well block (Qiagen, Valencia, Calif.) with each well containing 1–5 mL BTZ-3 containing kanamycin (50 µg/mL). The block was covered with a microporous tape sheet (Airpore™ film; Qiagen) and incubated in an AnaeroPack™ System (Mitsubishi Gas Chemical Co., Inc., Tokyo, Japan) filled with 25% methane as the sole carbon source. The AnaeroPack™ was shaking at 250 rpm for 2–3 days at 30° C.

Nitrate Medium for *Methylomonas* 16a

Nitrate liquid medium, also referred to herein as "defined medium" or "BTZ-3" medium was comprised of various salts mixed with Solution 1 as indicated below (Tables 2 and 3); or, where specified, the nitrate was replaced with 15 mM ammonium chloride. Solution 1 provides the composition for a 100 fold concentrated stock solution of trace minerals.

TABLE 2

Solution 1*

|  | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 3

Nitrate liquid medium (BTZ-3)**

|  | MW | Conc. (mM) | g per L |
|---|---|---|---|
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 |  | 50 mL |
| Solution 1 |  |  | 10 mL |

**Dissolve in 900 mL $H_2O$. Adjust to pH = 7, and add $H_2O$ to give 1 L. For agar plates: Add 15 g of agarose in 1 L of medium, autoclave, let cool down to 50° C., mix, and pour plates.

Carotenoid Determination

Cells were pelleted by centrifugation at 4000 g for 15 min, and the cell pellets were extracted with 10 mL acetone. The extraction was dried under nitrogen and redissolved in 1–2 mL of acetone. The extraction was filtered with an Acrodisc® CR25 mm syringe filter (Pall Corporation, Ann Arbor, Mich.). It was then concentrated in 0.1 mL 10% acetone+90% acetonitrile for HPLC analysis using an Agilent Series 1100 LC/MSD SI (Agilent, Foster City, Calif.).

Samples (20 µL) were loaded onto a 150 mm×4.6 mm ZORBAX C18 (3.5 µm particles) column (Agilent Technologies, Inc., Palo Alto, Calif.). The column temperature was kept at 40° C. The flow rate was 1 mL/min, while the solvent running program used was 0–2 min: 95% Buffer A and 5% Buffer B;

2–10 min: linear gradient from 95% Buffer A and 5% Buffer B to 60% Buffer A and 40% Buffer B;

10–12 min: linear gradient from 60% Buffer A and 40% Buffer B to 50% Buffer A and 50% Buffer B;

12–18 min: 50% Buffer A and 50% Buffer B; and,

18–20 min: 95% Buffer A and 5% Buffer B.

Buffer A was 95% acetonitrile and 5% $dH_2O$; Buffer B was 100% tetrahydrofuran. The mass spectrometer was

Example 1

Isolation of *Methylomonas* sp. 16a

The original environmental sample containing the isolate was obtained from pond sediment. The pond sediment was inoculated directly into defined medium with ammonium as the nitrogen source under 25% methane in air. Methane was the sole source of carbon and energy. Growth was followed until the optical density at 660 nm was stable, whereupon the culture was transferred to fresh medium such that a 1:100 dilution was achieved. After 3 successive transfers with methane as the sole carbon and energy source, the culture was plated onto BTZ-3 agar with ammonium as nitrogen source and incubated under 25% methane in air. Many methanotrophic bacterial species were isolated in this manner. However, *Methylomonas* sp. 16a was selected as the organism to study due to its rapid growth of colonies, large colony size, ability to grow on minimal media, and pink pigmentation indicative of an active biosynthetic pathway for carotenoids. *Methylomonas* sp. 16a has been deposited to the American Type Culture Collection (ATCC) under accession number PTA-2402 (deposited Aug. 22, 2000; see U.S. Pat. No. 6,689,601).

Example 2

Genomic Sequencing of *Methylomonas* sp. 16a

Genomic DNA was isolated from *Methylomonas* sp. 16a according to standard protocols. Genomic DNA and library construction were prepared according to published protocols (Fraser et al., *Science*, 270 (5235):397–403 (1995)). A cell pellet was resuspended in a solution containing 100 mM Na-EDTA pH 8.0, 10 mM Tris-HCl pH 8.0, 400 mM NaCl, and 50 mM $MgCl_2$.

Genomic DNA preparation After resuspension, the cells were gently lysed in 10% SDS (sodium dodecyl sulfate), and incubated for 30 min at 55° C. After incubation at room temperature, proteinase K was added to 100 µg/mL and incubated at 37° C. until the suspension was clear. DNA was extracted twice with Tris-equilibrated phenol and twice with chloroform. DNA was precipitated in 70% ethanol and resuspended in a solution containing 10 mM Tris-HCl and 1 mM Na-EDTA (TE), pH 7.5. The DNA solution was treated with a mix of RNAases, then extracted twice with Tris-equilibrated phenol and twice with chloroform. This was followed by precipitation in ethanol and resuspension in TE.

Library construction: 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb or 5.0 kb) was excised and cleaned, and a two-step ligation procedure was used to produce a high titer library with greater than 99% single inserts.

Sequencing: A shotgun sequencing strategy approach was adopted for the sequencing of the whole microbial genome (Fleischmann, R. et al., *Science* 269(5223):496–512 (1995)). Sequence was generated on an ABI Automatic sequencer using dye terminator technology (U.S. Pat. No. 5,366,860; EP 272,007) using a combination of vector and insert-specific primers. Sequence editing was performed in either DNAStar (DNA Star Inc.) or the Wisconsin GCG program (Wisconsin Package Version 9.0, Genetics Computer Group (GCG), Madison, Wis.) and the CONSED package (version 7.0). All sequences represent average of 8X coverage in both directions.

Example 3

Identification of Bacterial Hemoglobin Genes from *Methylomonas*

All sequences from Example 2 were identified by conducting BLAST (Basic Local Alignment Search Tool; Altschul, S. F., et al., *J. Mol. Biol.*, 215:403–410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W., and States, D. J., *Nature Genetics*, 3:266–272 (1993)) provided by the NCBI. All comparisons were done using either the BLASTNnr or BLASTXnr algorithm.

The results of these BLAST comparisons are given below in Table 4 for the present genes. Table 4 summarizes the sequence to which each *Methylomonas* gene has the most similarity (presented as % similarities, % identities, and expectation values). The table displays data based on the BLASTXnr algorithm with values reported in expect values. The Expect value estimates the statistical significance of the match, specifying the number of matches, with a given score, that are expected in a search of a database of this size absolutely by chance.

Three bacterial hemoglobin genes were identified in the genome of *Methylomonas* sp. 16a. They all belong to the family of truncated hemoglobins. Two of them (thbN1 and thbN2) belong to the group I truncated hemoglobins. The third one (thbO) belong to the group II truncated hemoglobins. The top hit of BLAST search for thbN1 was to a cyanobacterial globin family protein in *Methylococcus capsulatus* Bath (81% amino acid identity). The top hit of BLAST search for thbN2 was to the same cyanobacterial globin family protein in *Methylococcus capsulatus* Bath (64% amino acid identity). The thbN1 and thbN2 genes from *Methylomonas* sp. 16a share 69% amino acid identity and 65% nucleotide identity between each other. However, they share no significant homology with the group II truncated hemoglobin thbO (<17–20% amino acid identities). The top hit of BLAST search for thbO was to a conserved hypothetical protein in *Methylococcus capsulatus* Bath (62% amino acid identity). The thbO gene shares ~50% amino acid identities to a putative globin from *Bdellovibrio bacteriovorus* and to truncated hemoglobins from *Rubrivivax gelatinosus* and *Ralstonia metallidurans*.

TABLE 4

| ORF Name | Gene Name | Similarity Identified | SEQ ID | SEQ ID peptide | % Identity[a] | % Similarity[b] | E-value[c] | Citation |
|---|---|---|---|---|---|---|---|---|
| 1 | tHbN1 | gb\|AAU91352.1\| Cyanobacterial globin family protein [*Methylococcus capsulatus* strain Bath] | 1 | 2 | 81 | 89 | e-49 | Ward, N. et al PLoS Biol.2 (10), E303 (2004) |
| 2 | tHbN2 | gb\|AAU91352.1\| Cyanobacterial globin family protein [*Methylococcus capsulatus* strain Bath] | 3 | 4 | 64 | 73 | e-38 | Ward, N. et al PLoS Biol.2 (10), E303 (2004) |
| 3 | thbO | gb\|AAU91861.1\| Conserved hypothetical protein [*Methylococcus capsulatus* strain Bath] | 5 | 6 | 62 | 74 | 2e-40 | Ward, N. et al PLoS Biol.2 (10), E303 (2004) |

[a] % Identity is defined as percentage of amino acids that are identical between the two proteins.
[b] % Similarity is defined as percentage of amino acids that are identical or conserved between the two proteins.
[c] Expect value. The Expect value estimates the statistical significance of the match, specifying the number of matches, with a given score, that are expected in a search of a database of this size absolutely by chance. % Identity, % similarity, and e-values are all reported according to BLAST analysis.

Example 4

**Expression of *Methylomonas* Hemoglobin Genes in Recombinant *E. coli***

The thbN1, thbN2 and thbO genes were PCR amplified from the genomic DNA of *Methylomonas* sp. 16a using primers listed in Table 5. The PCR conditions were as follows: 5 min at 95° C.; then 35 cycles at 92° C. for 1 min, 55° C. for 1 min, and 72° C. for 1 min; followed by additional 10 min at 72° C. Underlined in the primer sequences are the incorporated SpeI sites. The 400 bp–450 bp PCR products were gel purified and cloned into pTrcHis2-TOPO® TA vector (Invitrogen), resulting in plasmids pDCQ385TA, pDCQ386TA and pDCQ387TA. *E. coli* DH10B cells containing these plasmids appear red on LB plates, indicating expression of the hemoglobin genes. The color of cells containing pDCQ385TA (expressing thbN1) and pDCQ386TA (expressing thbN2) was darker than cells containing pDCQ387TA (expressing thbO).

The Phps1 promoter (also referred to herein as the "hps" promoter; SEQ ID NO: 7) was amplified from *Methylomonas* 16a genomic DNA using the upstream primer 5'-CCATGGGCTAGCTAAGGATTGGGGTGCGT-3' (SEQ ID NO: 8) and the downstream primer 5'-CCATGGACTAGTGTGATGTGCTCCGAAAGT-3' (SEQ ID NO: 9). Underlined are the NcoI and NheI sites incorporated at the upstream end and the NcoI and SpeI sites incorporated at the downstream end. The 288 bp NcoI fragment containing Phps1 was cloned into the NcoI site of pBHR1 resulting pDCQ363. The SpeI fragments containing the thbN1, thbN2 and thbO genes were subcloned from the above three plasmids into the SpeI site of pDCQ363 plasmid, resulting in plasmids pDCQ385, pDCQ386 and pDCQ387. This set of plasmids contained the hemoglobin genes expressed on the lower copy number broad host range vector pBHR1 (MoBiTec, Goettingen, Germany). *E. coli* 10G strains containing these plasmids were also red, however, the color was lighter comparing to the genes expressed from the higher copy number pTrcHis2-TOPO® vector (Invitrogen).

TABLE 5

Primer sequences used in amplification of the hemoglobin genes from *Methylomonas* sp. 16a

| Name | Length (nt) | Oligo Sequence / (SEQ ID NOs.) |
|---|---|---|
| gbN1-16a-F | 34 | <u>ACTAGT</u>ACAAGCAGAGGAAAATCATTATGAGTGC (SEQ ID NO: 10) |
| gbN1-16a-R | 27 | <u>ACTAGT</u>TAGCGACCCAATACGTCGGTG (SEQ ID NO: 11) |
| gbN2-16a-F | 31 | <u>ACTAGT</u>AACTATGAGGATGCTATGAGCGAAG (SEQ ID NO: 12) |
| gbN2-16a-R | 26 | <u>ACTAGT</u>CTACTTTCCTAAGACCTCGC (SEQ ID NO: 13) |
| gbO-16a-F | 43 | <u>ACTAGT</u>AAGGAGGAATAAACCATGTCAGCACAAACGCCCTATG (SEQ ID NO: 14) |
| gbO-16a-R | 28 | <u>ACTAGT</u>CAACTTCGATCGTCTGCGGTAC (SEQ ID NO: 15) |

The underlined sequences are the incorporated SpeI sites. The bold sequences indicate the positions of the start and stop codons of the hemoglobin sequences.

Example 5

**Effect of *Methylomonas* Hemoglobin Gene Expression on *E. coli* Final Cell Density**

Figure 3A:
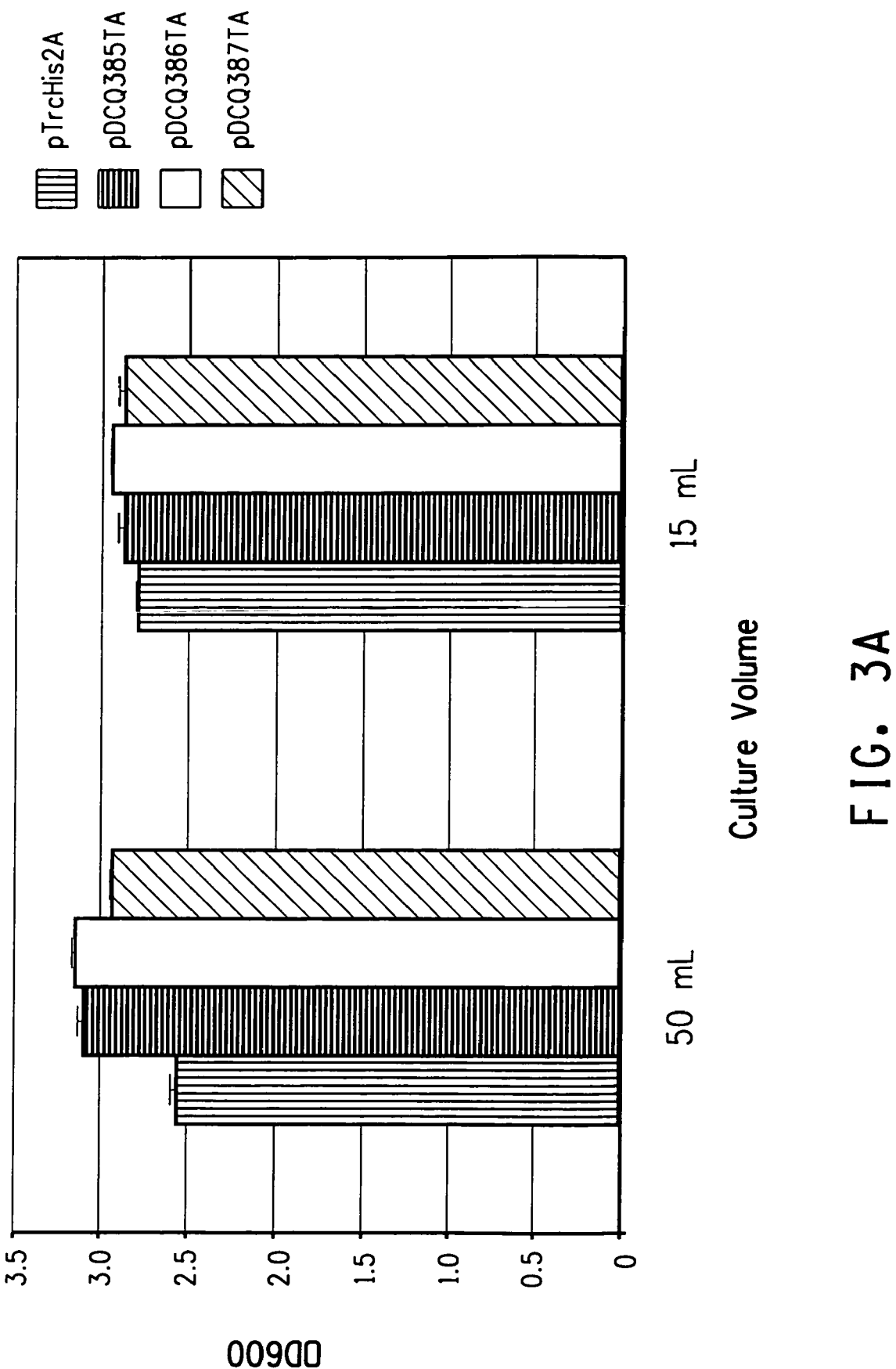
FIG. 3 shows the growth effects of recombinant bacterial hemoglobins expressed in *E. coli* from the expression vector pTrcHis2-TOPO® (top panel) or pBHR1 vector (bottom panel).
Figure 3B:
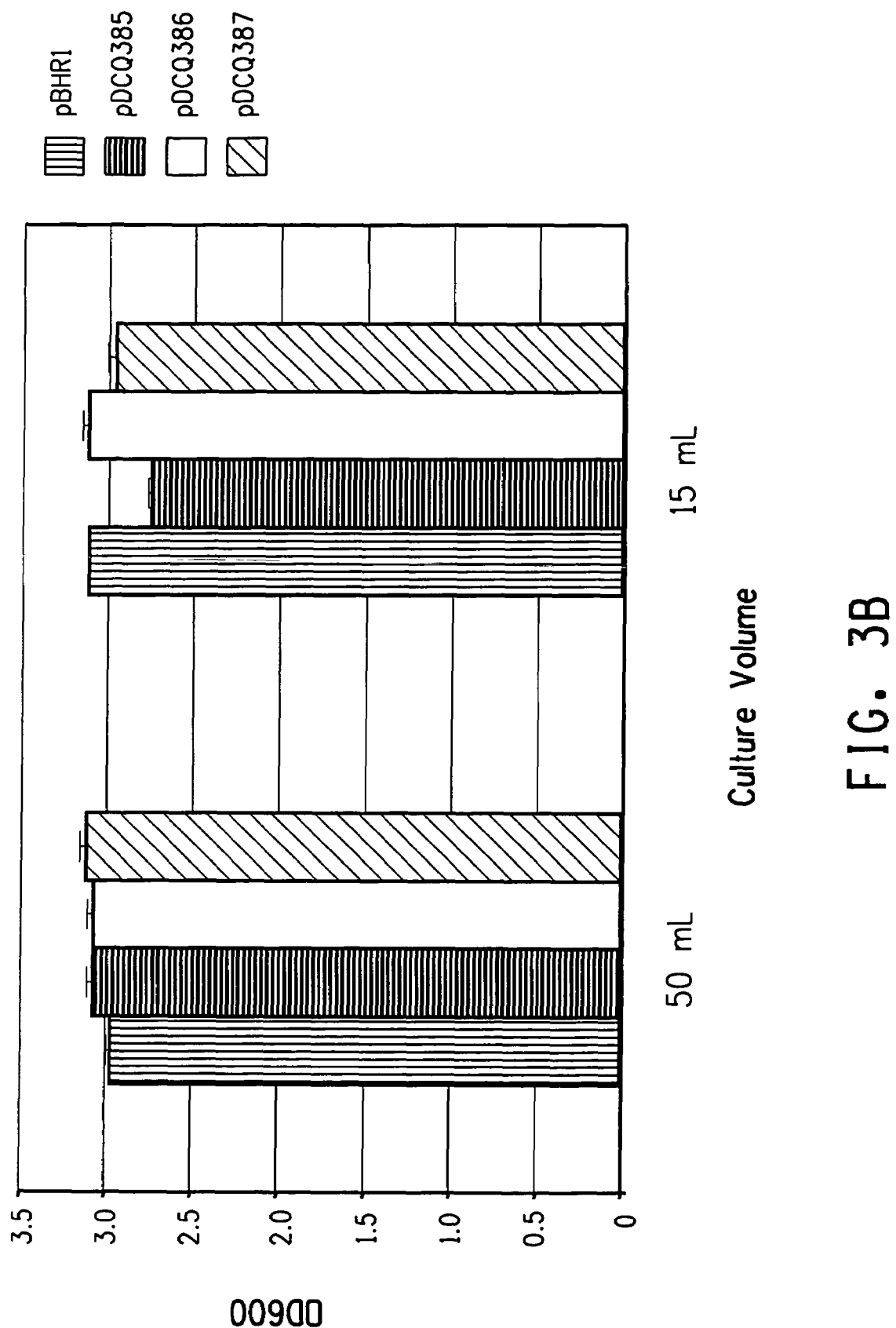

*E. coli* cells expressing the heterologous hemoglobin genes were compared with the cells containing the vector control for final cell density. *E. coli* DH10B cells containing pDCQ385TA, pDCQ386TA, pDCQ387TA or pTrcHis2A (pTrcHis2A is a circular version of pTrcHis2-TOPO®. The pTrcHis2-TOPO® vector is a linearized vector ready for ligation) were grown at 37° C. shaking 250 rpm overnight in 25 mL LB with 100 µg/mL ampicillin in 125-mL flasks. *E. coli* 10G cells containing pDCQ385, pDCQ386, pDCQ387 or pBHR1 were grown at 37° C. shaking 250 rpm overnight in 25 mL LB with 50 µg/mL kanamycin in 125-mL flasks. The $OD_{600}$ of the overnight cultures was adjusted to 2.5 and diluted 1:100 with fresh growth media. The diluted cultures were aliquoted to 50 mL/125 mL flask or 15 mL/125 mL flask in triplicates. The cultures were grown at 37° C. shaking 250 rpm for 24 hours. At the end of incubation, 0.1 mL culture was diluted with 0.9 mL LB and measured for $OD_{600}$. The data for the final cell density ($OD_{600}$) of the cultures were shown in FIG. 3. Top panel showed that on high copy number expression vector, thbN1 and thbN2 clones exhibited approximately 15% higher final cell density, whereas thbO clone exhibited approximately 7% higher final cell density comparing to the vector control strain when growing under oxygen limiting condition (50 mL culture volume). The increase of final cell density was much less (3–5%) when growing under oxygen sufficient condition (15 mL culture volume). When the hemoglobin genes were expressed on the low copy number vector (bottom panel), approximately 6% higher final cell density was observed under oxygen limiting condition and no correlation was observed under oxygen sufficient condition.

Example 6

Effect of Multicopy Expression of Hemoglobin Genes in *Methylomonas* on Astaxanthin Production A *Methylomonas* astaxanthin-producing strain (*Methylomonas* strain AX1-8) containing carotenoid synthesis genes integrated in the chromosome was used as the host to evaluate the effect of over-expression of hemoglobin genes on the astaxanthin production. Briefly, *Methylomonas* strain AX1-8 was created by chromosomally-integrating into *Methylomonas* sp. orihps333: 1) a crtWZ gene cluster into the ald genomic region (U.S. Ser. No. 10/997,844), and 2) an additional copy of a crtZ carotenoid hydroxylase gene into the tig genomic region (U.S. Ser. No. 11/070,080).

Briefly, the a nucleic acid molecule comprising the crtWZ coding regions was PCR amplified using primer pair HY-109 (5'-GGCCATGCCAATTGACTAGAAAGGAG-GMTAAACCATGACCGTCGAT CACGACGCA-3'; SEQ ID NO: 16) and HY-107 (5'-CGCGTACGCCTAGGTCAG-GCGCCGTTGCTGGATGAGCCGCGT-3'; SEQ ID NO: 17) from the carotenoid gene cluster crtWZEYIB found in plasmid pDCQ343 (SEQ ID NO: 18; U.S. Ser. No. 11/227, 663; herein incorporated by reference). The amplified fragment was digested with MfeI+AvrII, then cloned into the integration plasmid pAldcrtNhps at the MfeI and AvrII sites, operably linking the crtWZ coding regions to the hps promoter and creating plasmid pAldcrtNhps-WZ(343). *Methylomonas* sp. orihps333 was transformed with the integration plasmid, where integration the crtWZ cluster (operably linked to an hps promoter) occurred at the ald region, resulting in *Methylomonas* strain orihps333-AldhpsWZ. The coding region of an additional crtZ carotenoid hydroxylase gene was PCR amplified from crt cluster 343 using primer pair HY-117 (5'-CCATGCGMTTCACTA-GAAAGGAGGMTAAACCATGTCCTGGCCGAC GATG-3'; SEQ ID NO: 19) and HY-118 (5'-GACTGAAT-TCTCAGGCGCCGTTGCTGGATGAGCCGCGT-3'; SEQ ID NO: 20), digested with EcoRI, and cloned into the integration plasmid pTig at the EcoRI site, creating integration plasmid pTigcrtZ(343). *Methylomonas* strain orihps333-AldhpsWZ was transformed with integration plasmid pTigcrtZ(343), where the additional crtZ gene was integrated into the tig region, creating *Methylomonas* strain AX1-8.

The hemoglobin expression clones pDCQ385, pDCQ386, pDCQ387 and pBHR1 vector were introduced into the *Methylomonas* strain by tri-parental conjugation. The *E. coli* 10G donor strains containing these plasmids and an *E. coli* helper strain containing pRK2013 (ATCC No. 37159) were grown overnight in LB medium containing kanamycin (50 µg/mL), washed three times in LB, and resuspended in a volume of LB representing approximately a 60-fold concentration of the original culture volume. *Methylomonas* sp. AX-1 recipient strain was grown in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total-volume) at 30° C. with constant shaking. The donor, helper, and recipient cell pastes were combined in ratios of 1:1:2, respectively, on the surface of BTZ-3 agar plates containing 0.5% (w/v) yeast extract. Plates were maintained at 30° C. in 25% methane for 16–72 hours to allow conjugation to occur, after which the cell pastes were collected and resuspended in BTZ-3. Dilutions were plated on BTZ-3 agar containing kanamycin (50 µg/mL) and incubated at 30° C. in 25% methane for up to 1 week. Orange-red transconjugants were streaked onto BTZ-3 agar with kanamycin (50 µg/mL). The purified transconjugants were grown in a 24-well block (Qiagen) with each well containing 1–4 mL BTZ-3 containing kanamycin (50 µg/mL). The block was covered with Airpore™ film (Qiagen) and incubated in a sealed container such as the AnaeroPack™ System (Mitsubishi Gas Chemical Co., Inc., Japan) filled with 25% methane as the sole carbon source. The AnaeroPack™ was shaking at 250 rpm for 2–3 days at 30° C. The cells were pelleted by centrifugation and carotenoids in the cell pellets were analyzed by HPLC.

Figure 4A:
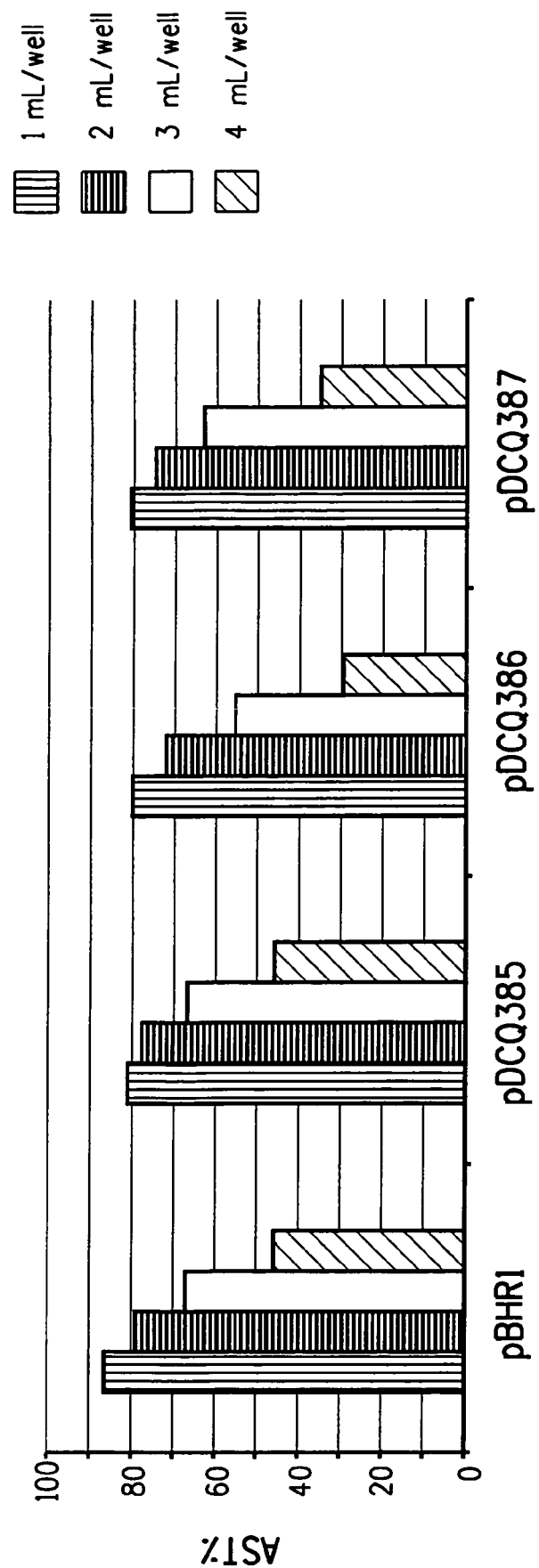
FIG. 4 shows the effects of multicopy expression of bacterial hemoglobins in *Methylomonas* sp. on astaxanthin selectivity ("AST %"; top panel) and relative astaxanthin amount (relative amount based on peak area of HPLC results normalized by cell density; bottom panel).
Figure 4B:
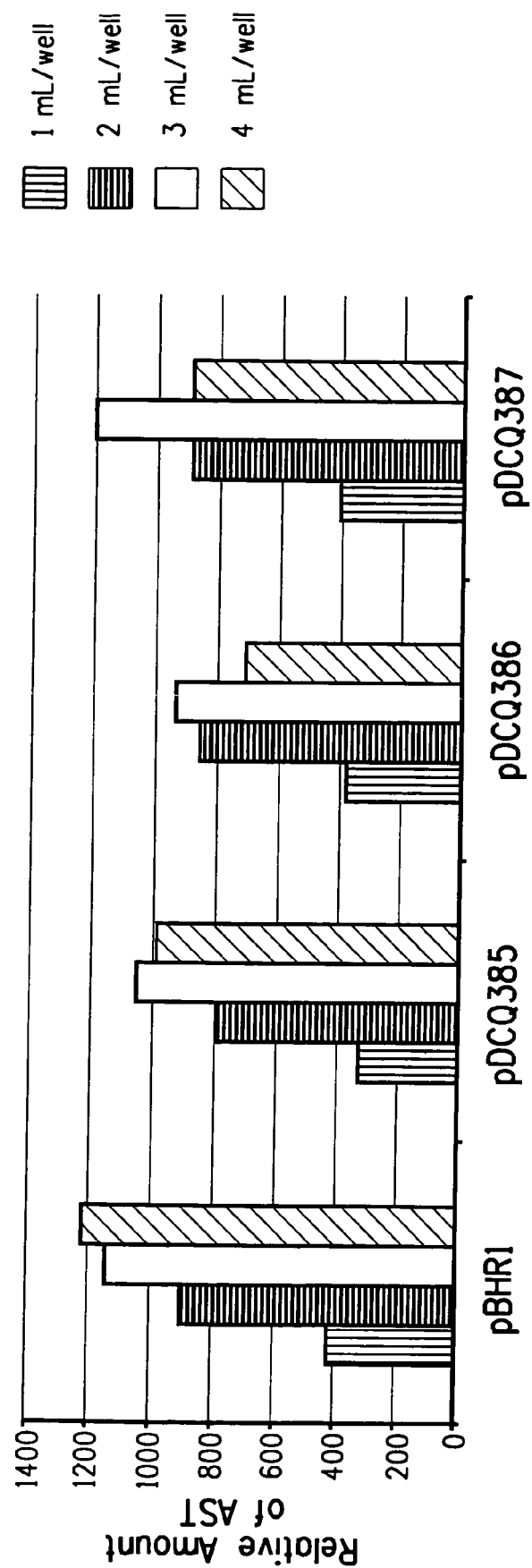

When cells were grown in 1 mL/well, efficient gas transfer allowed sufficient oxygen for the cells. All the strains produced >80% astaxanthin in the total carotenoids. When the culture volume increased per well, oxygen became limited for the cells due to inefficient gas transfer and astaxanthin production decreased (FIG. 4).

Example 7

Effect of Multicopy Expression of Hemoglobin Genes with the crtWZ in *Methylomonas* on Astaxanthin Production In Example 6, it is shown that overexpression of hemoglobins alone on plasmids did not significantly improve astaxanthin production when overexpressed in a carotenogenic host cell having two chromosomally-integrated CrtW ketolase and CrtZ hydroxylase genes. This limited effect observed on carotenoid production may have been attributed to the relative low expression levels of the ketolase and hydroxylase genes (both require molecular oxygen for their respective activities) on the chromosome. Here the hemoglobin genes with additional crtWZ genes were overexpressed on multicopy plasmids, and compared with overexpression of crtWZ only control on plasmids to determine if hemoglobins could improve the function: of the oxygen-requiring CrtWZ to improve astaxanthin production.

Plasmid pDCQ365 (U.S. Ser. No. 11/200,394) containing the crtW from *Sphingomonas melonis* DC18 (U.S. Ser. No. 11/015,433; SEQ ID NO: 21) and the crtZ from *Novosphingobium aromaticivorans* (U.S. Ser. No. 11/200,394; SEQ ID NO: 22) expressed under an endogenous *Methylomonas* promoter Phps1 (U.S. Ser. No. 10/689,200; SEQ ID NO: 7). The *Methylomonas* hemoglobin genes thbN1, thbN2 or thbO were cut out as SpeI fragments from pDCQ385TA, pDCQ386TA or pDCQ387TA and cloned upstream of the crtWZ in pDCQ365. The resulted plasmid, pDCQ393, comprises thbN1 co-expressed with crtWZ. The resulted plasmid pDCQ394 comprises thbN2 co-expressed with crtWZ. The resulted plasmid pDCQ391 comprises thbO co-expressed with crtWZ. *Methylomonas* strain AX1-8 (an astaxanthin producing strain) was used as the host to evaluate the effect of co-expression of hemoglobin genes with crtWZ on the astaxanthin conversion. The hemoglobin and crtWZ co-expression clones pDCQ393, pDCQ394, pDCQ391 and the pDCQ365 and pBHR1 controls were introduced into the *Methylomonas* strain AX1-8 by tri-parental conjugation. The *E. coli* 10G donor strains containing these plasmids and an *E. coli* helper strain containing pRK2013 (ATCC No. 37159) were grown overnight in LB medium containing kanamycin (50 µg/mL), washed three times in LB, and resuspended in a volume of LB representing approximately a 60-fold concentration of the original culture volume. *Methylomonas* sp. AX1-8 recipient strain was grown in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume) at 30° C. with constant shaking. The donor, helper, and recipient cell pastes were combined in ratios of 1:1:2, respectively, on the surface of BTZ-3 agar plates containing 0.5% (w/v) yeast extract. Plates were maintained at 30° C. in 25% methane for 16–72 hours to allow conjugation to occur, after which the cell pastes were collected and resuspended in BTZ-3. Dilutions were plated on BTZ-3 agar containing kanamycin (50 µg/mL) and incubated at 30° C. in 25% methane for up to 1 week. Orange-red transconjugants were streaked onto BTZ-3 agar with kanamycin (50 µg/mL). The purified transconjugants were grown in a 24-well block (Qiagen) with each well containing 1–5 mL BTZ-3 containing kanamycin (50 µg/mL). The block was covered with Airpore™ film (Qiagen) and incubated in an AnaeroPack™ System (Mitsubishi Gas Chemical Co.) filled with 25% methane as the sole carbon source. The AnaeroPack™ was shaking at 250 rpm for 2–3 days at 30° C. The cells were pelleted by centrifugation and carotenoids in the cell pellets were analyzed by HPLC as described above (FIG. 5).

Figure 5A:
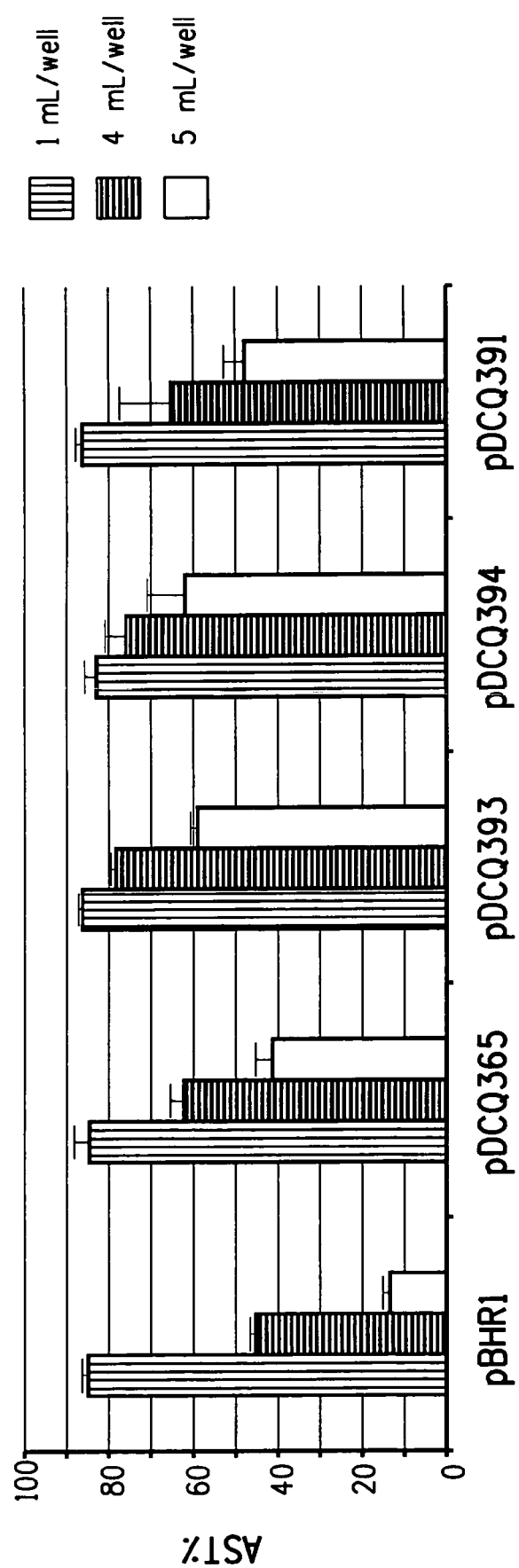
FIG. 5 shows the effects of multicopy expression of bacterial hemoglobins with the crtWZ in *Methylomonas* on astaxanthin selectivity ("AST %"; top panel) and relative astaxanthin amount (relative amount based on peak area of HPLC results normalized by cell density; bottom panel).
Figure 5B:
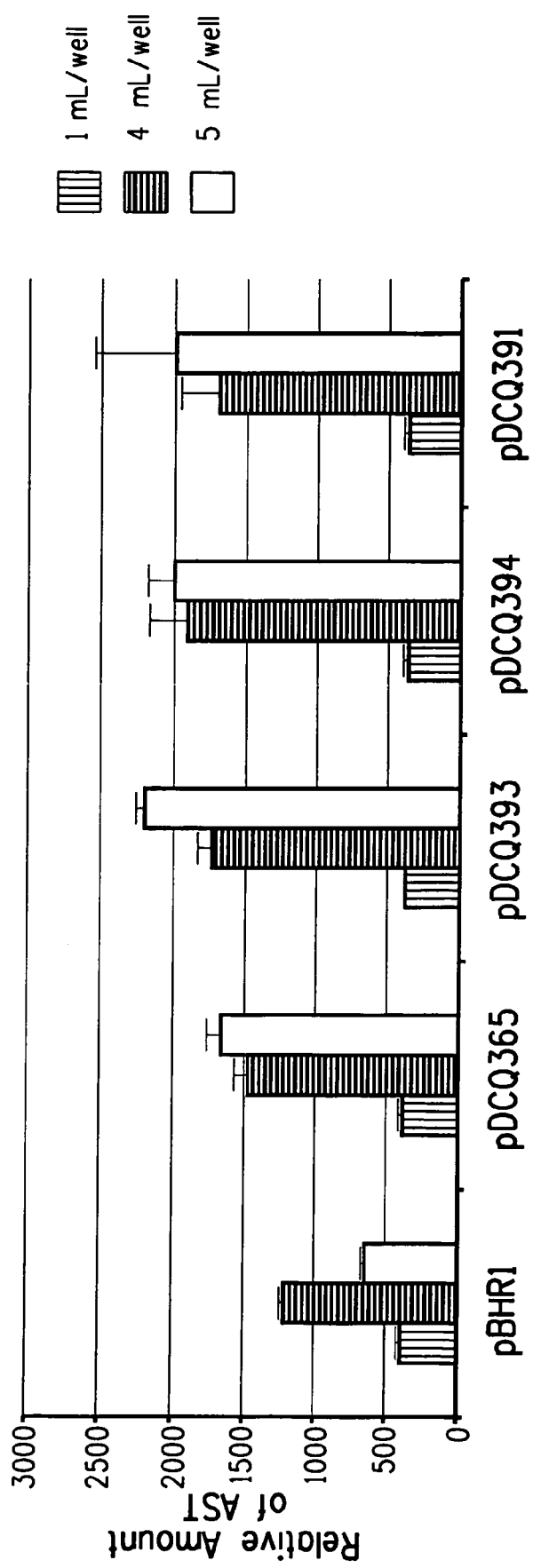

The top panel of FIG. 5 showed the astaxanthin selectivity, which is the percentage of astaxanthin in the total carotenoids produced. When cells were grown in 1 mL/well, efficient gas transfer allowed sufficient oxygen for the cells. All the strains produced >80% astaxanthin in the total carotenoids. When the culture volume increased per well, oxygen became limited for the cells due to inefficient gas transfer and astaxanthin production decreased. In the cases of growing 4 mL/well, strain containing the pBHR1 vector produced about 46% astaxanthin and the strain containing pDCQ365 expressing crtWZ produced about 62% astaxanthin. The strains containing pDCQ393 or pDCQ394 expressing the thbN1-crtWZ or thbN2-crtWZ produced close to 80% astaxanthin, whereas pDCQ391 expressing the thbO-crtWZ produced slightly higher percentage (about 65%) of astaxanthin. In the cases of growing 5 mL/well, strain containing the pBHR1 vector produced about 13% astaxanthin and the strain containing pDCQ365 expressing crtWZ produced about 42% astaxanthin. The strains containing pDCQ393 or pDCQ394 expressing the thbN1-crtWZ or thbN2-crtWZ produced about 60% astaxanthin, whereas pDCQ391 expressing the thbO-crtWZ produced slightly higher percentage (about 48%) of astaxanthin. The bottom panel of FIG. 5 showed the relative amount of astaxanthin produced in the strains. They were calculated from the area of astaxanthin peaks on HPLC normalized by cell densities. When cells were grown in 1 mL/well, the strains produced similar amount of astaxanthin. When cells were grown in 4 mL/well or 5 mL/well, strains co-expressed hemoglobins and CrtWZ produced higher amount of astaxanthin than the strains expressed the CrtWZ alone or the vector plasmid. Under the same growth conditions, the total carotenoids produced from the strains were similar. Hemoglobins most likely improved the activity of the oxygen-requiring CrtWZ enzymes for astaxanthin conversion, which enhanced the astaxanthin production.

---

What is claimed is:

1. An isolated nucleic acid molecule encoding an oxygen binding protein selected from the group consisting of:
   (a) an isolated nucleic acid molecule encoding a polypeptide having an amino acid sequence selected from the group consisting of SEQ ID NO:2, 4, and 6;
   (b) an isolated nucleic acid molecule that hybridizes with (a) under the following hybridization conditions: 0.1X SSC, 0.1% SDS, 65° C. and washed with 2X SSC, 0.1% SDS followed by 0.1X SSC, 0.1% SDS, 65° C.;
   (c) an isolated nucleic acid molecule encoding a polypeptide having an amino acid sequence having at least 95% identity to an amino acid sequence selected from the group consisting of SEQ ID NO: 2, 4, and 6; and
   (d) An isolated nucleic acid that is fully complementary to the full-length sequence (a), (b), or (c).

2. The isolated nucleic acid molecule according to claim 1 selected from the group consisting of SEQ ID NO: 1, 3, and 5.

3. An isolated transformed host cell comprising the isolated nucleic acid molecule of claim 1.

4. The transformed host cell of claim 3 wherein the host cell is selected from the group consisting of bacteria, yeast, filamentous fungi, and algae.

5. The transformed host cell of claim 4 wherein the host cell is selected from the group consisting of *Aspergillus, Trichoderma, Saccharomyces, Pichia, Phaffia, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

6. The transformed host cell of claim 4 wherein the host cell is a methylotrophic bacteria.

7. The transformed host cell of claim 6 wherein the methylotrophic bacteria is a methanotrophic bacteria.

8. The transformed host cell of claim 7 wherein methanotrophic bacteria is *Methylomonas* sp. 16a (ATCC PTA-2402) or a derivative thereof.

* * * * *